(12) United States Patent
Nitzan

(10) Patent No.: US 11,406,393 B2
(45) Date of Patent: Aug. 9, 2022

(54) METHODS AND DEVICES FOR REDUCING PRESSURE

(71) Applicant: White Swell Medical Ltd, Kibbutz Shefayim (IL)

(72) Inventor: Yaacov Nitzan, Hertzelia (IL)

(73) Assignee: White Swell Medical Ltd, Kibbutz Shefayim (IL)

( * ) Notice: Subject to any disclaimer, the term of this patent is extended or adjusted under 35 U.S.C. 154(b) by 256 days.

(21) Appl. No.: 16/493,167

(22) PCT Filed: Mar. 19, 2018

(86) PCT No.: PCT/IB2018/000364
§ 371 (c)(1),
(2) Date: Sep. 11, 2019

(87) PCT Pub. No.: WO2018/172848
PCT Pub. Date: Sep. 27, 2018

(65) Prior Publication Data
US 2020/0046372 A1 Feb. 13, 2020

Related U.S. Application Data

(60) Provisional application No. 62/473,420, filed on Mar. 19, 2017.

(51) Int. Cl.
*A61B 17/132* (2006.01)
*A61B 17/12* (2006.01)
*A61B 17/135* (2006.01)

(52) U.S. Cl.
CPC ........ *A61B 17/1325* (2013.01); *A61B 17/135* (2013.01); *A61B 17/12036* (2013.01)

(58) Field of Classification Search
CPC .............. A61B 17/1325; A61B 17/135; A61B 17/12036; A61B 17/12109
(Continued)

(56) References Cited

U.S. PATENT DOCUMENTS 3,211,150 A 10/1965 Foderick
3,926,175 A 12/1975 Allen et al.
(Continued)

FOREIGN PATENT DOCUMENTS

EP 0526102 A1 2/1993
EP 2353501 A1 8/2011
(Continued)

OTHER PUBLICATIONS

Stone, Michael et al. The Effect of Rigid Cervical Collars on Internal Jugular Vein Dimensions. Academic Emergency Medicine, vol. 17, No. 1, Jan. 4, 2010, pp. 100-102 [pdf online], [retrieved on Jul. 29, 2021], Retrieved from the Internet <URL:https://onlinelibrary.wiley.com/ > (Year: 2010).*
(Continued)

*Primary Examiner* — Katherine H Schwiker
*Assistant Examiner* — Serenity A Miller
(74) *Attorney, Agent, or Firm* — Brown Rudnick LLP; Adam M. Schoen

(57) ABSTRACT

The disclosure provides device and related methods that can be used to treat edema by applying pressure to a blood vessel such as a jugular vein to restrict flow therein, creating a local decrease in blood pressure within the jugular vein near an outlet of a lymphatic duct, causing lymph to drain from the interstitium.

9 Claims, 25 Drawing Sheets

(58) Field of Classification Search
USPC .................................................... 606/202
See application file for complete search history.

(56) References Cited

U.S. PATENT DOCUMENTS

| | | |
|---|---|---|
| 4,714,460 A | 12/1987 | Calderon |
| 4,822,341 A | 4/1989 | Colone |
| 4,838,864 A | 6/1989 | Peterson |
| 4,957,484 A | 9/1990 | Murtfeldt |
| 5,005,564 A | 4/1991 | Grundei et al. |
| 5,069,662 A | 12/1991 | Bodden |
| 5,097,840 A | 3/1992 | Wallace et al. |
| 5,366,504 A | 11/1994 | Andersen et al. |
| 5,391,143 A | 2/1995 | Kensey |
| 5,484,412 A | 1/1996 | Pierpont |
| 5,509,897 A | 4/1996 | Twardowski et al. |
| 5,554,119 A | 9/1996 | Harrison et al. |
| 5,558,642 A | 9/1996 | Schweich, Jr. et al. |
| 5,716,340 A | 2/1998 | Schweich, Jr. et al. |
| 5,817,046 A | 10/1998 | Glickman |
| 5,836,912 A | 11/1998 | Kusleika |
| 5,893,841 A | 4/1999 | Glickman |
| 5,897,533 A | 4/1999 | Glickman |
| 5,908,407 A | 6/1999 | Frazee et al. |
| 5,919,163 A | 7/1999 | Glickman |
| 5,921,913 A | 7/1999 | Siess |
| 6,042,569 A | 3/2000 | Finch, Jr. et al. |
| 6,139,517 A | 10/2000 | Macoviak et al. |
| 6,152,945 A | 11/2000 | Bachinski et al. |
| 6,165,196 A | 12/2000 | Stack et al. |
| 6,179,796 B1 | 1/2001 | Waldridge |
| 6,183,492 B1 | 2/2001 | Hart et al. |
| 6,248,091 B1 | 6/2001 | Voelker |
| 6,254,563 B1 | 7/2001 | Macoviak et al. |
| 6,503,224 B1 | 1/2003 | Forman et al. |
| 6,524,323 B1 | 2/2003 | Nash et al. |
| 6,555,057 B1 | 4/2003 | Bendera |
| 6,616,623 B1 | 9/2003 | Kutushov |
| 6,635,068 B1 | 10/2003 | Dubrul et al. |
| 6,699,231 B1 | 3/2004 | Sterman et al. |
| 6,878,140 B2 | 4/2005 | Barbut |
| 6,936,057 B1 | 8/2005 | Nobles |
| 7,022,097 B2 | 4/2006 | Glickman |
| 7,195,608 B2 | 3/2007 | Burnett |
| 7,645,259 B2 | 1/2010 | Goldman |
| 7,766,892 B2 | 8/2010 | Keren et al. |
| 7,780,628 B1 | 8/2010 | Keren et al. |
| 8,109,880 B1* | 2/2012 | Pranevicius ............ A61B 5/021 |
| | | 600/490 |
| 8,126,538 B2 | 2/2012 | Shuros et al. |
| 8,216,122 B2 | 7/2012 | Kung |
| 8,480,555 B2 | 7/2013 | Kung |
| 8,679,057 B2 | 3/2014 | Fulton, III et al. |
| 9,179,921 B1 | 11/2015 | Morris |
| 9,405,942 B2 | 8/2016 | Liao et al. |
| 9,421,316 B2 | 8/2016 | Leeflang et al. |
| 9,433,713 B2 | 9/2016 | Corbett et al. |
| 9,486,566 B2 | 11/2016 | Siess |
| 9,533,054 B2 | 1/2017 | Yan et al. |
| 9,533,084 B2 | 1/2017 | Siess et al. |
| 9,642,991 B2 | 5/2017 | Eversull et al. |
| 9,669,142 B2 | 6/2017 | Spanier et al. |
| 9,669,144 B2 | 6/2017 | Spanier et al. |
| 9,675,739 B2 | 6/2017 | Tanner et al. |
| 9,682,223 B2 | 6/2017 | Callaghan et al. |
| 9,750,861 B2 | 9/2017 | Hastie et al. |
| 9,770,543 B2 | 9/2017 | Tanner et al. |
| 9,878,080 B2 | 1/2018 | Kaiser et al. |
| 9,901,722 B2 | 2/2018 | Nitzan et al. |
| 10,149,684 B2 | 12/2018 | Nitzan et al. |
| 10,154,846 B2 | 12/2018 | Nitzan et al. |
| 10,195,405 B2 | 2/2019 | Nitzan et al. |
| 10,207,086 B2 | 2/2019 | Nitzan et al. |
| 10,226,604 B2 | 3/2019 | Nitzan et al. |
| 10,226,605 B2 | 3/2019 | Nitzan et al. |
| 10,245,363 B1 | 4/2019 | Rowe |
| 10,285,708 B2 | 5/2019 | Nitzan et al. |
| 10,300,254 B2 | 5/2019 | Nitzan et al. |
| 10,639,460 B2 | 5/2020 | Nitzan et al. |
| 10,653,871 B2 | 5/2020 | Nitzan et al. |
| 10,709,878 B2 | 7/2020 | Nitzan et al. |
| 10,912,873 B2 | 2/2021 | Nitzan et al. |
| 10,926,069 B2 | 2/2021 | Nitzan et al. |
| 10,960,189 B2 | 3/2021 | Nitzan et al. |
| 2003/0093109 A1 | 5/2003 | Mauch |
| 2003/0134416 A1 | 7/2003 | Yamanishi et al. |
| 2004/0006306 A1 | 1/2004 | Evans et al. |
| 2004/0064091 A1 | 4/2004 | Keren et al. |
| 2004/0147871 A1 | 7/2004 | Burnett |
| 2004/0210296 A1 | 10/2004 | Schmitt et al. |
| 2004/0230181 A1 | 11/2004 | Cawood |
| 2005/0228474 A1 | 10/2005 | Laguna |
| 2005/0251180 A1 | 11/2005 | Burton et al. |
| 2006/0030814 A1 | 2/2006 | Valencia et al. |
| 2006/0064059 A1 | 3/2006 | Gelfand et al. |
| 2006/0100658 A1 | 5/2006 | Obana et al. |
| 2006/0161095 A1 | 7/2006 | Aboul-Hosn et al. |
| 2006/0178604 A1 | 8/2006 | Alderman |
| 2007/0055299 A1 | 3/2007 | Ishimaru et al. |
| 2007/0282303 A1 | 12/2007 | Nash et al. |
| 2007/0282382 A1 | 12/2007 | Shuros et al. |
| 2008/0009719 A1 | 1/2008 | Shuros et al. |
| 2008/0015628 A1 | 1/2008 | Dubrul et al. |
| 2008/0071135 A1 | 3/2008 | Shaknovich |
| 2008/0097412 A1 | 4/2008 | Shuros et al. |
| 2008/0103573 A1 | 5/2008 | Gerber |
| 2008/0140000 A1 | 6/2008 | Shuros et al. |
| 2008/0294228 A1 | 11/2008 | Brooke et al. |
| 2009/0018526 A1 | 1/2009 | Power et al. |
| 2009/0112184 A1 | 4/2009 | Fierens et al. |
| 2009/0131785 A1 | 5/2009 | Lee et al. |
| 2010/0168649 A1 | 7/2010 | Schwartz et al. |
| 2010/0179389 A1 | 7/2010 | Moroney, III et al. |
| 2010/0280451 A1 | 11/2010 | Teeslink et al. |
| 2011/0004046 A1 | 1/2011 | Campbell et al. |
| 2011/0092955 A1 | 4/2011 | Purdy et al. |
| 2011/0257462 A1 | 10/2011 | Rodefeld et al. |
| 2011/0276023 A1 | 11/2011 | Leeflang et al. |
| 2011/0282274 A1 | 11/2011 | Fulton, III |
| 2011/0295302 A1 | 12/2011 | Mohl |
| 2012/0029466 A1 | 2/2012 | Callaghan et al. |
| 2012/0157913 A1 | 6/2012 | Aziz et al. |
| 2012/0259215 A1 | 10/2012 | Gerrans et al. |
| 2013/0096476 A1* | 4/2013 | Rogachevsky ......... A61F 5/042 |
| | | 602/18 |
| 2013/0096494 A1 | 4/2013 | Kassab |
| 2013/0138041 A1 | 5/2013 | Smisson, III et al. |
| 2013/0237954 A1 | 9/2013 | Shuros et al. |
| 2013/0245607 A1 | 9/2013 | Eversull et al. |
| 2013/0317535 A1 | 11/2013 | Demmy |
| 2013/0338559 A1 | 12/2013 | Franano et al. |
| 2014/0010686 A1 | 1/2014 | Tanner et al. |
| 2014/0128659 A1 | 5/2014 | Heuring et al. |
| 2014/0142616 A1 | 5/2014 | Smith |
| 2014/0155815 A1 | 6/2014 | Fulton, III et al. |
| 2014/0220617 A1 | 8/2014 | Yung et al. |
| 2014/0243790 A1 | 8/2014 | Callaghan et al. |
| 2014/0249386 A1 | 9/2014 | Caron et al. |
| 2014/0296615 A1 | 10/2014 | Franano |
| 2014/0303461 A1 | 10/2014 | Callaghan et al. |
| 2014/0336551 A1 | 11/2014 | Mantese et al. |
| 2014/0358036 A1 | 12/2014 | Holmes |
| 2015/0051634 A1 | 2/2015 | Kravik et al. |
| 2015/0157777 A1 | 6/2015 | Tuval et al. |
| 2015/0164662 A1 | 6/2015 | Tuval |
| 2015/0238671 A1 | 8/2015 | Mesallum |
| 2015/0283360 A1 | 10/2015 | Kelly |
| 2015/0343136 A1 | 12/2015 | Nitzan et al. |
| 2015/0343186 A1 | 12/2015 | Nitzan et al. |
| 2016/0022890 A1 | 1/2016 | Schwammenthal et al. |
| 2016/0045203 A1 | 2/2016 | Pollock |
| 2016/0051741 A1 | 2/2016 | Schwammenthal et al. |
| 2016/0129266 A1 | 5/2016 | Schmidt |
| 2016/0169630 A1 | 6/2016 | Augustine et al. |

(56) References Cited

U.S. PATENT DOCUMENTS

| | | |
|---|---|---|
| 2016/0213826 A1 | 7/2016 | Tanner et al. |
| 2016/0331378 A1 | 11/2016 | Nitzan et al. |
| 2017/0014563 A1 | 1/2017 | Khir |
| 2017/0095395 A1* | 4/2017 | Wennen .......... A41D 1/00 |
| 2017/0197021 A1 | 7/2017 | Nitzan et al. |
| 2017/0224512 A1 | 8/2017 | Hingston |
| 2017/0319764 A1 | 11/2017 | Tanner et al. |
| 2018/0125499 A1 | 5/2018 | Nitzan et al. |
| 2018/0126130 A1 | 5/2018 | Nitzan et al. |
| 2018/0146968 A1 | 5/2018 | Nitzan et al. |
| 2018/0185622 A1 | 7/2018 | Nitzan et al. |
| 2018/0193614 A1 | 7/2018 | Nitzan et al. |
| 2018/0193615 A1 | 7/2018 | Nitzan et al. |
| 2018/0193616 A1 | 7/2018 | Nitzan et al. |
| 2018/0250456 A1 | 9/2018 | Nitzan et al. |
| 2019/0014991 A1* | 1/2019 | Maki .......... A61B 5/1079 |
| 2019/0046706 A1 | 2/2019 | Aboul-Hosn et al. |
| 2019/0046707 A1 | 2/2019 | Aboul-Hosn et al. |
| 2019/0083761 A1 | 3/2019 | Nitzan et al. |
| 2019/0117943 A1 | 4/2019 | Nitzan et al. |
| 2019/0117944 A1 | 4/2019 | Nitzan et al. |
| 2019/0126014 A1 | 5/2019 | Kapur et al. |
| 2019/0167878 A1 | 6/2019 | Rowe |
| 2019/0223877 A1 | 7/2019 | Nitzan et al. |
| 2019/0366063 A1 | 12/2019 | Nitzan et al. |
| 2020/0016383 A1 | 1/2020 | Nitzan et al. |
| 2020/0046372 A1 | 2/2020 | Nitzan |
| 2020/0206485 A1 | 7/2020 | Nitzan et al. |
| 2020/0230380 A1 | 7/2020 | Nitzan et al. |
| 2020/0230381 A1 | 7/2020 | Nitzan et al. |
| 2020/0268951 A1 | 8/2020 | Nitzan et al. |
| 2020/0268952 A1 | 8/2020 | Nitzan et al. |
| 2020/0268954 A1 | 8/2020 | Nitzan et al. |
| 2020/0269025 A1 | 8/2020 | Nitzan et al. |
| 2020/0276369 A1 | 9/2020 | Nitzan et al. |
| 2020/0306436 A1 | 10/2020 | Tanner et al. |
| 2020/0397963 A1 | 12/2020 | Nitzan et al. |
| 2021/0121678 A1 | 4/2021 | Nitzan et al. |

FOREIGN PATENT DOCUMENTS

| | | |
|---|---|---|
| EP | 2353503 A1 | 8/2011 |
| EP | 2637927 A1 | 9/2013 |
| WO | 89/04193 A1 | 5/1989 |
| WO | 01/013983 A2 | 3/2001 |
| WO | 2012/135834 A2 | 10/2012 |
| WO | 2013/025826 A1 | 2/2013 |
| WO | 2013/061281 A1 | 5/2013 |
| WO | 2014/141284 A2 | 9/2014 |
| WO | 2015/186003 A2 | 12/2015 |
| WO | 2017/087556 A1 | 5/2017 |
| WO | 2018172848 A2 | 9/2018 |

OTHER PUBLICATIONS

International Search Report and Written Opinion dated Apr. 12, 2018, for PCT/IB17/01488, filed Oct. 31, 2017 (11 pages).

International Search Report and Written Opinion dated Jun. 25, 2018, for PCT/IB18/00263, filed Mar. 1, 2018 (10 pages).

International Search Report and Written Opinion dated Oct. 30, 2018, for PCT/IB18/000364, filed Mar. 19, 2018 (9 pages).

Non-Final Office Action issued in U.S. Appl. No. 15/799,562, dated Jul. 28, 2020 (8 pages).

Non-Final Office Action issued in U.S. Appl. No. 15/870,111, dated Jun. 24, 2020 (5 pages).

Non-Final Rejection issued in U.S. Appl. No. 16/867,047, dated Sep. 16, 2020 (11 pages).

International Search Report and Written Opinion dated Oct. 30, 2018, for PCT/IB18/00364, filed Mar. 19, 2018 (10 pages).

Bannon, 2011, Anatomic considerations for central venous cannulation, Risk Manag Healthc Policy 4:27-39.

Moscucci, 2014, Section III Hemodynamic principles 10 Pressure measurement, 223-244 in Grossman & Baim's Cardiac Catheterization, Angiography, and Intervention 8 Ed.

Shimizu, 2014, Embolization of a fractured central venous catheter placed using the internal jugular apporach, Int J Surg Case Rep 5:219.

Swan, 1970, Catheterization of the Heart in Man with Use of a Flow-directed Balloon-tipped Catheter, NEJM 283(9):447-451.

Yancy, 2013, 2013 ACCF/AHA Guideline for the Management of Heart Failure, Circulation 128(16):e240-e327.

* cited by examiner

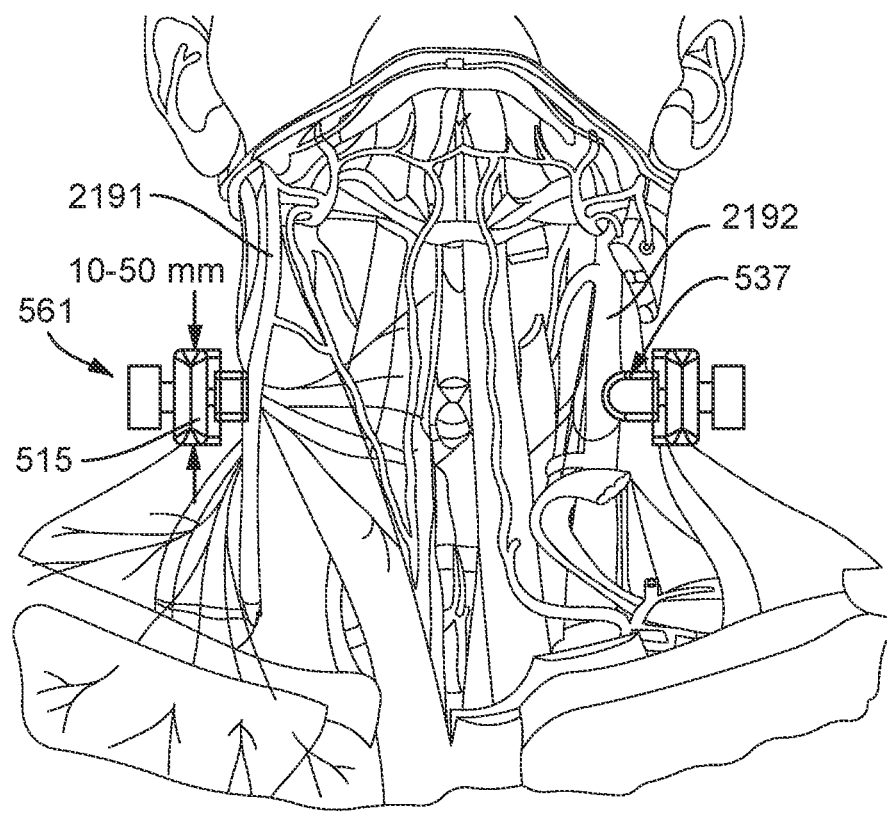
FIG. 7
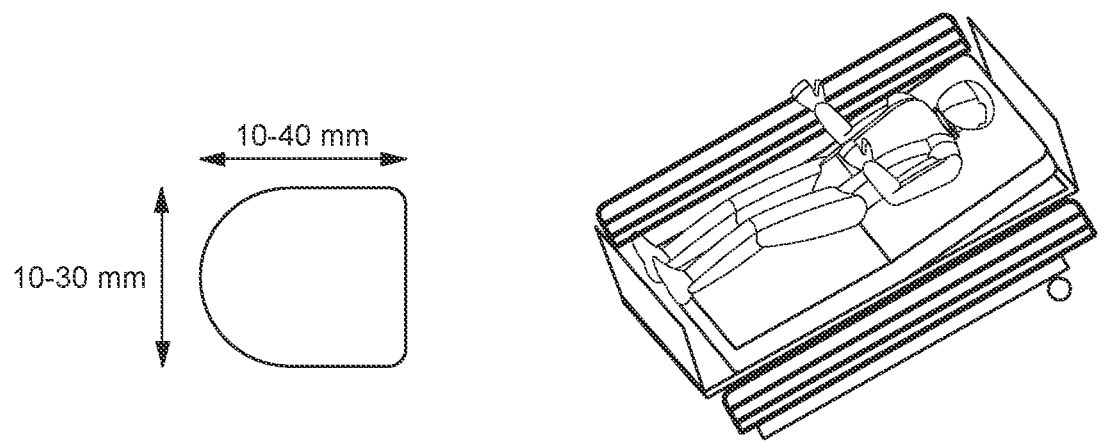
FIG. 8
FIG. 9

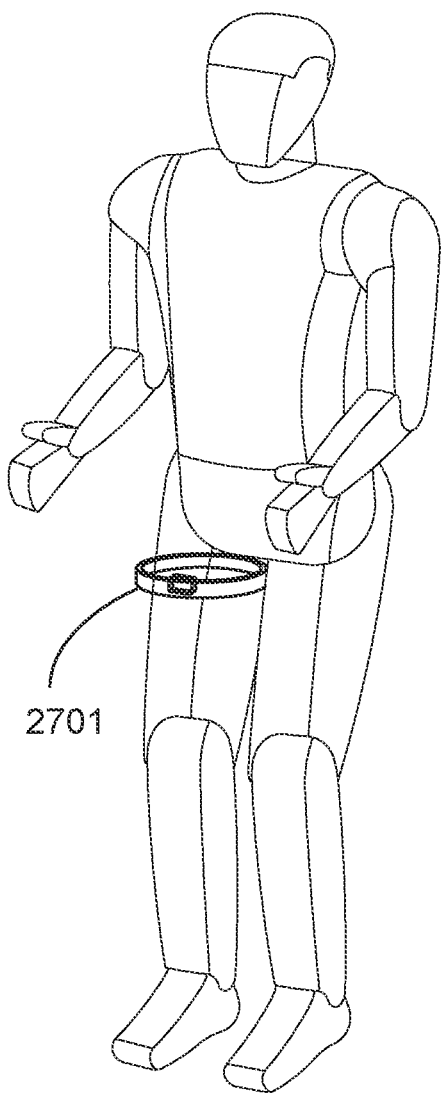
FIG. 28
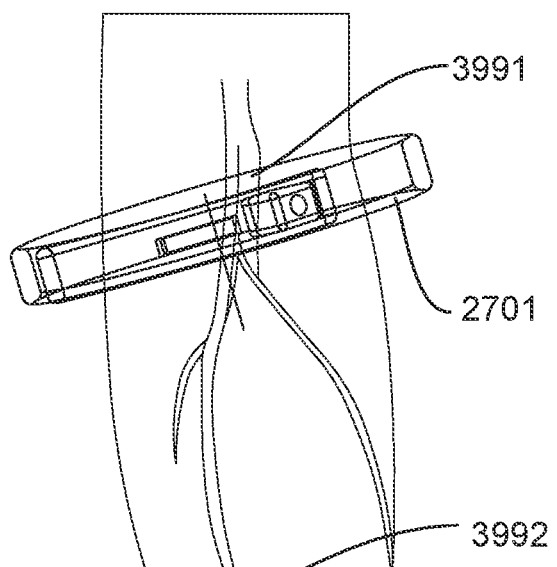
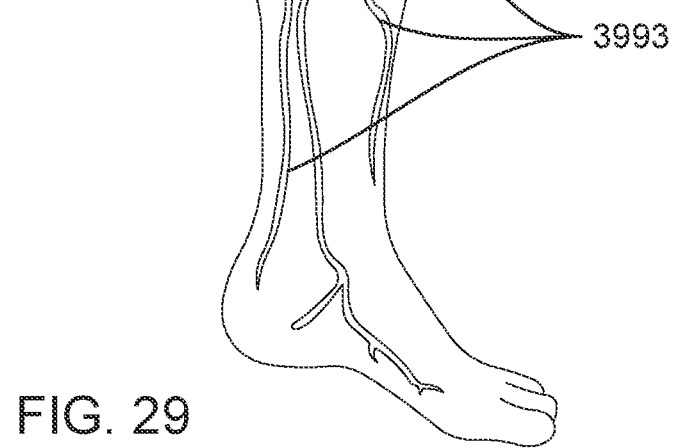
FIG. 29

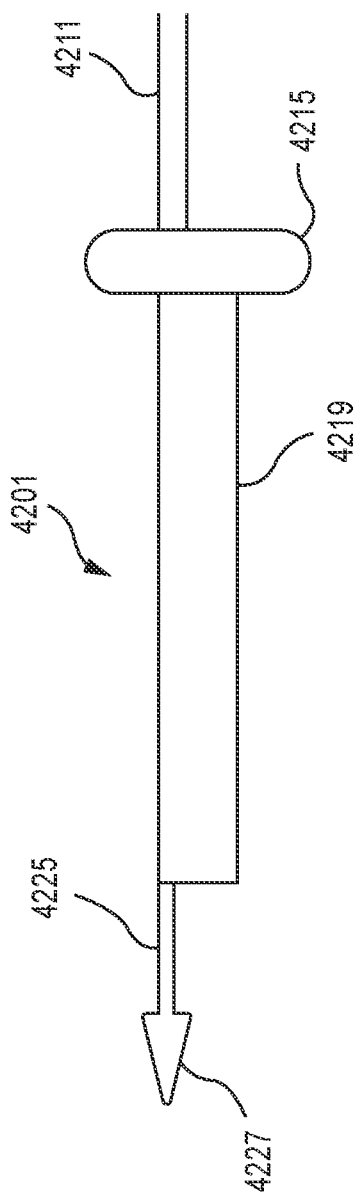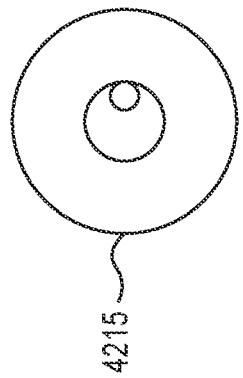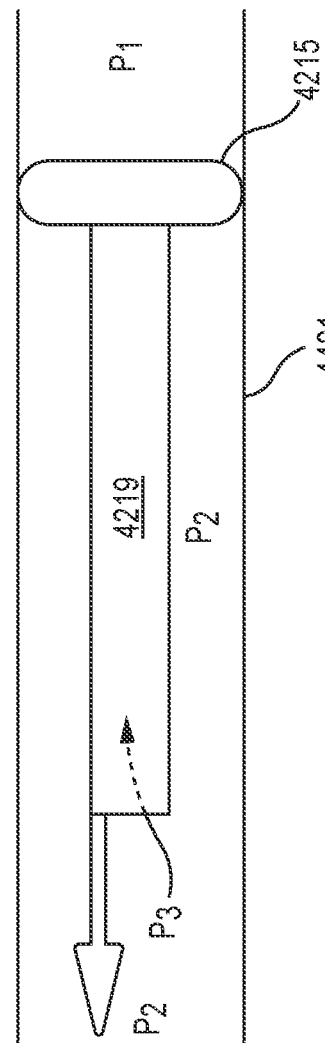

METHODS AND DEVICES FOR REDUCING PRESSURE

CROSS-REFERENCE TO RELATED APPLICATIONS

This application claims priority to U.S. Provisional Application No. 62/473,420, filed Mar. 19, 2017, the contents of which are incorporated by reference.

TECHNICAL FIELD

The disclosure relates to heart failure and edema.

BACKGROUND

Heart failure, often referred to as congestive heart failure (CHF), occurs when the heart is unable to pump sufficiently to maintain blood flow to meet the body's needs. A person suffering heart failure may experience shortness of breath, exhaustion, and swollen limbs. Heart failure is a common, costly, and potentially fatal condition. In 2015 it affected about 40 million people globally with around 2% of adults overall having heart failure. As many as 10% of people over the age of 65 are susceptible to heart failure.

In heart failure, the pressures in the heart ventricles and atria are excessively elevated. As a result, the heart works harder to eject blood, leading to a buildup of blood pressure, which may result in edema forming within interstitial compartments of the body. Edema refers to the abnormal accumulation of fluid in tissues of the body and results when elevated blood pressure prevents lymphatic fluid from draining from the interstitium. The additional work of the heart, with time, weakens and remodels the heart thus further reducing the ability of the heart to function properly. The fluid accumulation leads to dyspnea and acute decompensated heart failure (ADHF) hospitalization. Those conditions may result in severe health consequences including death.

SUMMARY

The disclosure provides device and related methods that can be used to treat edema by applying pressure to a blood vessel such as a jugular vein to restrict flow therein, creating a local decrease in blood pressure within the jugular vein near an outlet of a lymphatic duct, causing lymph to drain from the interstitium. A device for applying pressure may have the form of a neck cuff or similar, with an extended collar member that may extend around a neck of a patient, with a projection protruding inward from an inner surface of the collar member to press against the neck near the jugular vein, restricting blood flow within the jugular vein. Thus, the disclosure provides methods and devices for reducing pressure within the heart ventricle and as a result in the venous system and in the lymphatic outflow.

In certain aspects, the invention provides a device for treating edema. The device includes an extended collar member dimensioned to extend at least partway around a neck of a patient and a projection protruding inward from an inner surface of the collar member. The projection is positioned to press against the neck near a jugular vein, thereby restricting blood flow within the jugular vein. The extended collar member may be in the form of a neck cuff that fastens around the neck. The neck cuff may include an elongated, flexible strap with an adjustable fastening mechanism that allows the strap to be fastened into a closed loop at any of a plurality of circumferences. The projection may be provided as an elastic pad seated in the strap.

In some embodiments, the device includes a screw threaded through a portion of the collar member, wherein the projection is provided by a tip of the screw. Twisting a head of the screw when the extended collar member is disposed about the neck of the patient drives the projection into the neck to restrict flow within the jugular vein. The tip of the screw may include an elastic pad that, when the screw is tightened, restricts flow within the jugular vein. Restricting the flow within the jugular vein causes pressure near an outlet of a lymphatic duct to decrease.

In certain embodiments, the extended collar member includes a C-shaped semi-ring that extends about halfway around the neck. The semi-ring may include at least a first tang fastened at a first end of the semi-ring and extending therefrom. A screw may be threaded through the first tang, such that the projection is provided as an elastic pad disposed over an inner tip of the screw. An outer base of the screw may have wide head, e.g., textured or knurled for manipulation. Preferably, twisting the wide head of the screw when the extended collar member is disposed around the neck of the patient drives the elastic pad into the neck to restrict flow within the jugular vein. The semi-ring may also have a second tang fastened at a second end of the semi-ring and extending therefrom, the second tang having a second screw threaded therethrough. Thus, the extended collar member may include a rigid C-shaped semi-ring that extends at least partially around the neck, the semi-ring having at least a first tang extending from a first end of the semi-ring, wherein the projection protrudes inward from an inner surface of the first tang.

In some embodiments, the projection includes an inflatable pad. Inflating the pad when the extended collar member is disposed around the neck of the patient drives the pad into the neck to restrict flow within the jugular vein.

In certain embodiments, the extended collar member extends at least partially around the neck, and at least a portion of the collar member is inflatable, such that inflating the portion when the collar member is disposed around the neck of the patient drives the projection into the neck to restrict flow within the jugular vein.

In some embodiments, the extended collar member includes a releasable fastening mechanism defining a plurality of stops corresponding to progressively tighter fittings, wherein cinching the extended collar mechanism closed drives the projection into the neck to restrict flow within the jugular vein.

In related aspects, the disclosure provides a method of draining lymph. The method includes restricting flow through a jugular vein of a patient by applying pressure to a neck of the patient at a spot on the neck proximal to the jugular vein, thereby decreasing pressure at an outflow of a lymphatic duct. Methods may be used for reducing the pressures within the heart, especially during its diastolic phase, which may improve filling pattern of the ventricle and enable the AV valve to open at a later time in the isovolumetric relaxation phase of the heart cycle. That could in turn improve contractility of the heart. Furthermore, reducing the pressures during the diastolic phase, which is about 75% of the cardiac cycle, reduces the pressures throughout the venous system, thereby alleviating the edema formed by high venous and left ventricular filling pressures present in heart failure patients and in ADHF patients. The reduction of pressures in the venous system will in turn enhance lymphatic return because the outflow pressure in the thoracic and lymphatic ducts will be reduced. The thoracic duct empties into the venous system and in heart failure patients the central venous pressure (CVP) is high and therefore the lymphatic return is not as high as it could be if the CVP was reduced.

Methods of the disclosure are preferably used with a patient affected by heart failure or edema. Embodiments of the methods include applying the pressure to the spot on the neck by making contact between the spot on the neck and a medical device for treating edema. In some embodiments, methods use a device that includes an extended collar member dimensioned to extend at least partway around the neck with projection protruding inward from an inner surface of the collar member, the projection positioned to press against the spot on the neck.

BRIEF DESCRIPTION OF THE DRAWINGS

FIG. 7 is a close-up of the device with screws.
FIG. 8 shows an elastic pad of the device with screws.
FIG. 9 depicts a patient being treated with the device with screws.
FIG. 28 shows a patient with the limb-cuff device.
FIG. 29 shows the limb cuff device disposed with respect to a femoral vein.
FIG. 42 illustrates a collapsible tube device for treating edema.
FIG. 43 shows the balloon of the collapsible tube device.
FIG. 44 shows the collapsible tube device located within a vessel of a patient.

DETAILED DESCRIPTION

The disclosure provide devices and methods for reducing the pressures within the heart especially during its diastolic phase to provide improved filling pattern of the ventricle and enable the AV valve to open at a later time in the isovolumetric relaxation phase of the heart cycle. This may in turn improve contractility of the heart. Furthermore, reducing the pressures during the diastolic phase, which is about 75% of the cardiac cycle, may reduce the pressures throughout the venous system and thus alleviate the edema formed as a result of the excessively high venous and left ventricular filling pressures present in heart failure patients and in ADHF patients. The reduction of pressures in the venous system will in turn enhance lymphatic return because the outflow pressure in the thoracic and lymphatic ducts will be reduced. The thoracic duct empties into the venous system and in heart failure patients the central venous pressure (CVP) is high and therefore the lymphatic return is not as high as it could be if the CVP was reduced.

Figure 1:
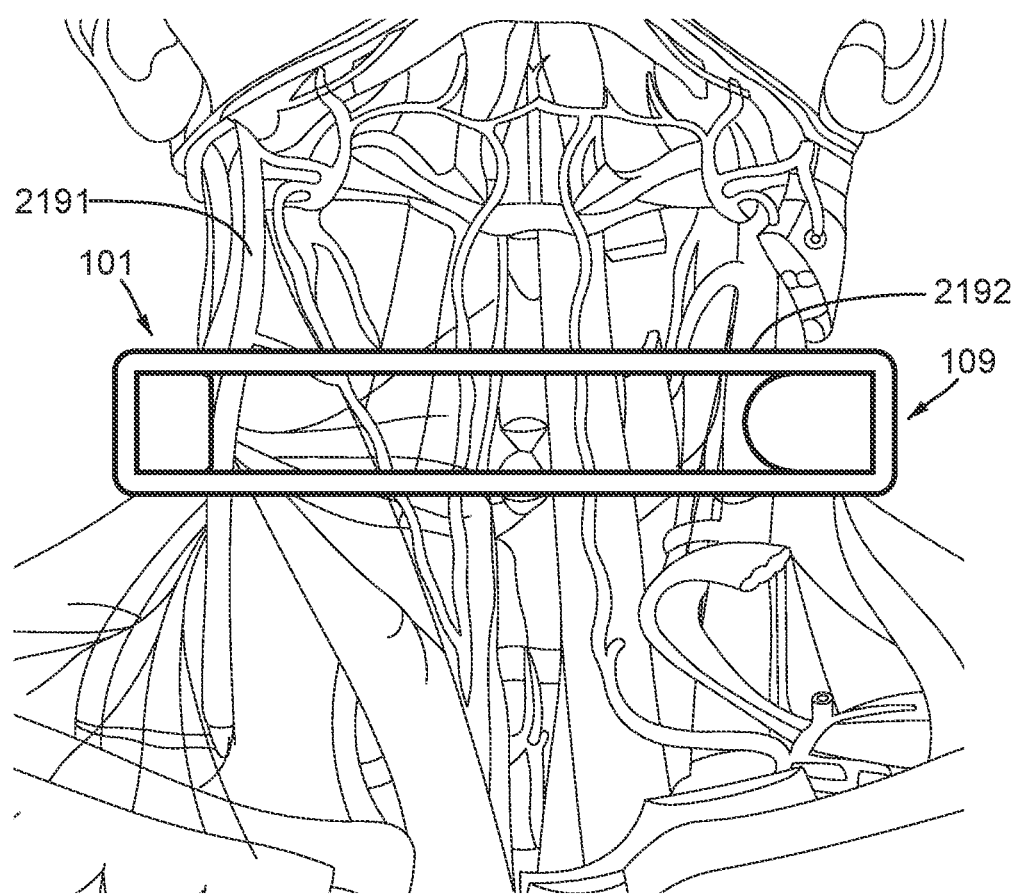
FIG. 1 shows a device for treating edema.

FIG. 1 shows a device 101 for treating edema, positioned with respect to an external jugular vein 2191 and an internal jugular vein 2192. The device 101 includes an extended collar member dimensioned to extend at least partway around a neck of a patient and a projection protruding inward from an inner surface of the collar member. The collar member may be provided as a strap 109. The projection is positioned to press against the neck near a jugular vein, thereby restricting blood flow within the jugular vein.

Figure 2:
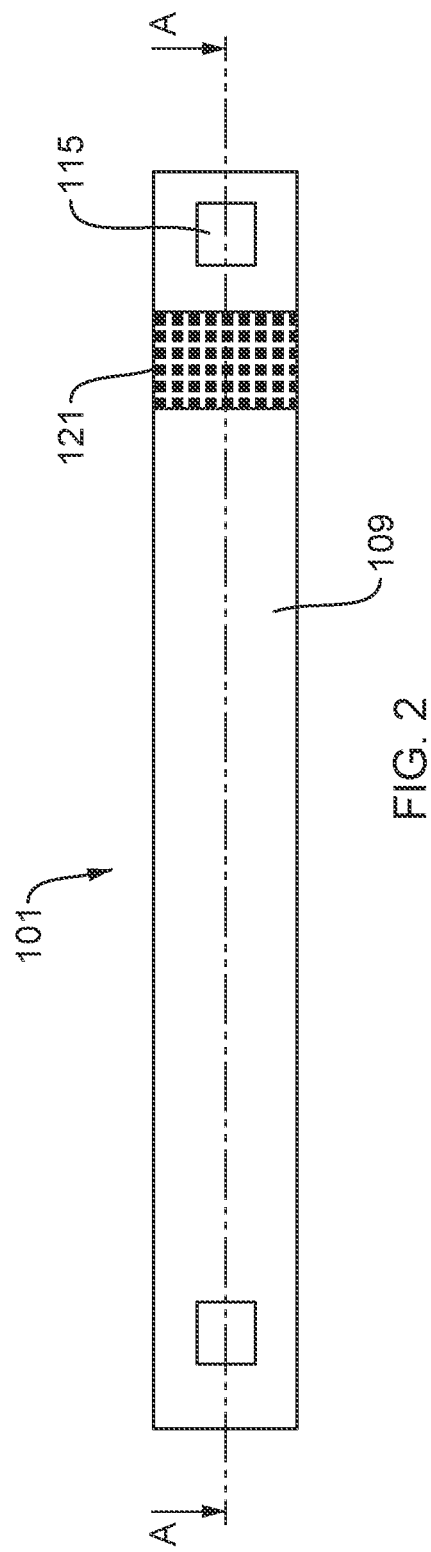
FIG. 2 is a top view of the neck brace device.

FIG. 2 is a top view of the neck brace device 101. Preferably, the neck cuff comprises an elongated, flexible strap 109 with an adjustable fastening mechanism 115 that allows the strap to be fastened into a closed loop at any of a plurality of circumferences. The device 101 includes a projection in the form of an elastic pad 121 seated in the strap 109.

Figure 3:
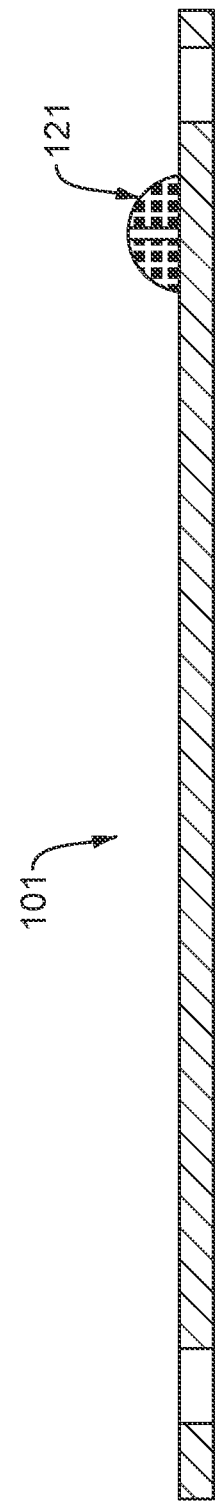
FIG. 3 is a side view of the device.

FIG. 3 shows a side view of the neck brace device 101. The device 101 is useful for reducing the pressure in the outflow of the lymphatic ducts and by that enhancing lymphatic return in fluid overloaded patients. In the depicted embodiment, the extended collar member forms a neck cuff that fastens around the neck.

Figure 4:
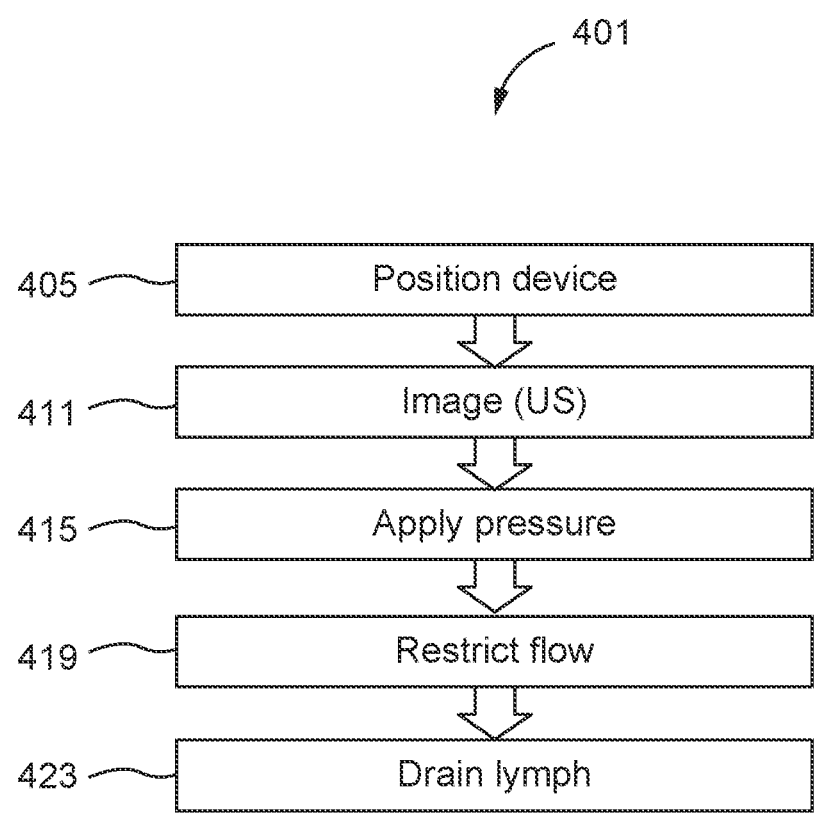
FIG. 4 diagrams a method of draining lymph.

FIG. 4 diagrams a method 401 of draining lymph. The method 401 includes positioning 405 a device at a neck of a patient. The method 401 may include imaging 411 the treatment location using a medical imaging instrument or technique such as ultrasound (US). The method 401 includes applying 415 pressure to a neck of the patient at a spot on the neck proximal to the jugular vein. This results in restricting 419 flow through a jugular vein of a patient by thereby decreasing pressure at an outflow of a lymphatic duct. As a result, lymph will drain 423 from the lymphatic system to the circulatory system. Preferably, the method 401 is used to treat a patient affected by heart failure or edema.

In some embodiments, applying 415 the pressure includes making contact between the spot on the neck and a medical device for treating edema, such as the device 101. The method 401 employs the functionality by which the heart is a suction pump that is constantly trying to preserve cardiac output. As such when the right atrium and ventricle detect a reduction or restriction in the return of blood to the right heart during the diastolic phase, the heart muscle will create more negative pressures in an attempt to compensate and pull in the required blood volume and maintain blood flow. Those phenomena of the heart are not necessarily impeded in heart failure patients but if they are impeded they still exist in a lesser extent. Nearly half of all patients with heart failure have a normal ejection fraction (EF). The prevalence of this syndrome, termed heart failure with preserved ejection fraction (HFpEF), continues to increase in the developed world, likely because of the increasing prevalence of common risk factors, including older age, female sex, hypertension, metabolic syndrome, renal dysfunction and obesity.

In heart failure patients, the systolic function can be impaired, the diastolic volume can be impaired in HFpEF patients but the basic ability of the heart muscle to create these negative pressures during the diastolic phase (if the return of blood to the atria is reduced) can still be functional. As a result of the suction mechanism of the right ventricle the overall venous pressure and central venous pressure (CVP) will be reduced as the venous system is directly connected to the right ventricle and atria during the diastole phase. The reduction of the CVP, when the heart increases its suction forces, can lead to improved medical condition in pathologies such as ADHF, reduced kidney filtration, edema, lymphedema, and lymphatic flow. All those pathologies rely on normal CVP in order to function optimally. For example, the reduced CVP will reduce the pressure at the lymphatic outflow both in the thoracic duct and the lymphatic duct. The method 401 may be useful to enhance the lymphatic return and alleviate edema that accompanies most of ADHF hospitalizations.

The method 401 may also reduce the pressures in the renal vein and in the rest of the venous system and thus alleviate the edema by allowing interstitial fluid to return into the venous system and in the lymph nodes, as well. Reducing the venous pressure in the renal vein can improve renal flow and thus improve renal function. Thus the disclosure provides devices, systems and methods for achieving those benefits, which devices, systems, and methods may be very beneficial for patients.

One way for achieving the suction effect of the heart and reduce its diastolic pressures can be to partially restrict the flow in any of the major veins such as the right or left jugular, right or left subclavian, femoral veins, or the inferior vena cava (IVC). The partial flow restriction can be achieved in several ways including but not limited to intravenous, extra venous, and transcutaneous devices which act to limit fluid flow. In some embodiments, a device is placed in or on a patient, activated and any level of restriction from full to partial restriction is achieved. As a result, the pressures in the venous system will be reduced and ADHF patients can be treated to alleviate the edema via both the lymphatic and venous systems drainage of interstitial edema.

As one example of a device of the disclosure, a transcutaneous device 101 for reducing CVP pressure is provided. The device 101 provides an externally applied compression probe that may be located on the patient's skin directly adjacent to a target vessel such as one of the internal jugular veins (IJVs). The right or left internal jugular veins are commonly accessed using the Seldinger technique on the left or right side of the patient's neck for the placement of central venous catheters. A needle and guidewire are advanced through patient's skin into the jugular vein and then a central venous catheter is advanced over the wire either posteriorly or proximally. Here, the compression probe (e.g., device 101) is applied in contact with the skin on the patient's neck. A portion of the compression probe consists of tip 121 which focally compresses the tissue adjacent to the target vessels (e. g. internal jugular) thereby effecting compression of the target vessel thereby reducing distal flow and pressure.

Since the left and right jugular vein are usually in close proximity to the carotid artery the device compression probe tip could have the form of a small hemi balloon inflated to say 40 mm Hg. Such a balloon would compress and occlude the jugular vein having typical pressure of <30 mm Hg without occluding the carotid (which would be extended by arterial blood pressure running upwards of 70 mm Hg). The compression probe can be made form a biocompatible material for example silicon and the rate of jugular constriction can be regulated by ultrasound visualization of the jugular and a confirmation of the pressure reduction by measuring the baseline and after restriction diameter of the opposite internal jugular. Once the probe compresses as desired the collar is then fixed in place and the restriction is maintained throughout the period of the treatment.

To target such a compression probe, ultrasound could be used in the same manner as for determining the site for a needle penetration for placement of a central line. Alternatively, the subject invention could include an ultrasound array integrated into the device. Such an array would enhance accuracy of device placement and also provide capability to monitor pressure and flow distal to the pressure tip.

The pressure probe may be mounted in something like a collar or harness to keep it in place for a considerable time, and the probe may be advanced carefully by one of several means, (e. g. adjustable screw thread or secondary pressure balloon). The compression probe balloon pressure could be displayed on a pressure gage that could be observed as the probe is advanced until an appropriate pressure was achieved (30-70 mm Hg). Devices of the disclosure may also include an integrated pressure/flow sensor (e.g. via ultrasound) which would allow dynamic closed loop adjustment of the compression probe to achieve the desired flow reduction. For example, the compression probe could be cycled on and off at varying intervals to vary the flow restriction and flow reduction and to further allow periods of normal flow.

In related embodiments, the restriction is achieved by a pressing on the femoral vein, similarly as may be done for the jugular vein. Devices and methods of the disclosure may also be used with intravascular edema catheters such as those disclosed in WO 2015/186003; WO 2015/186005; WO 2016/181217; U.S. Pub. 2017/0197021; and U.S. Pub. 2016/0331378, incorporated by reference.

The following approach may be suitable or preferable for some applications. As an example of an extravascular flow restrictor, a compression device can be advanced through the patient's skin to a site located adjacent the target vessel. The tip of the transcutaneous probe selectively applies pressure to the vessel. In one embodiment, the extravascular probe tip consists of an inflatable balloon.

Another extravascular flow restrictor comprises a compression cuff which is placed around the target vessel. Such a device could be placed surgically, percutaneously, or using minimally invasive techniques. A balloon element in the collar would allow selective compression of the target vessel, much like a blood pressure cuff. For patients that frequently suffer from pulmonary edema, such a device could consist of a long-term implant which can be activated by an implantable controller, much like a pacemaker, to adjust venous pressure as needed or prescribed by a physician.

The following embodiments may be useful for reducing the pressures by applying external forces that restrict the jugular vein flow.

Figure 5:
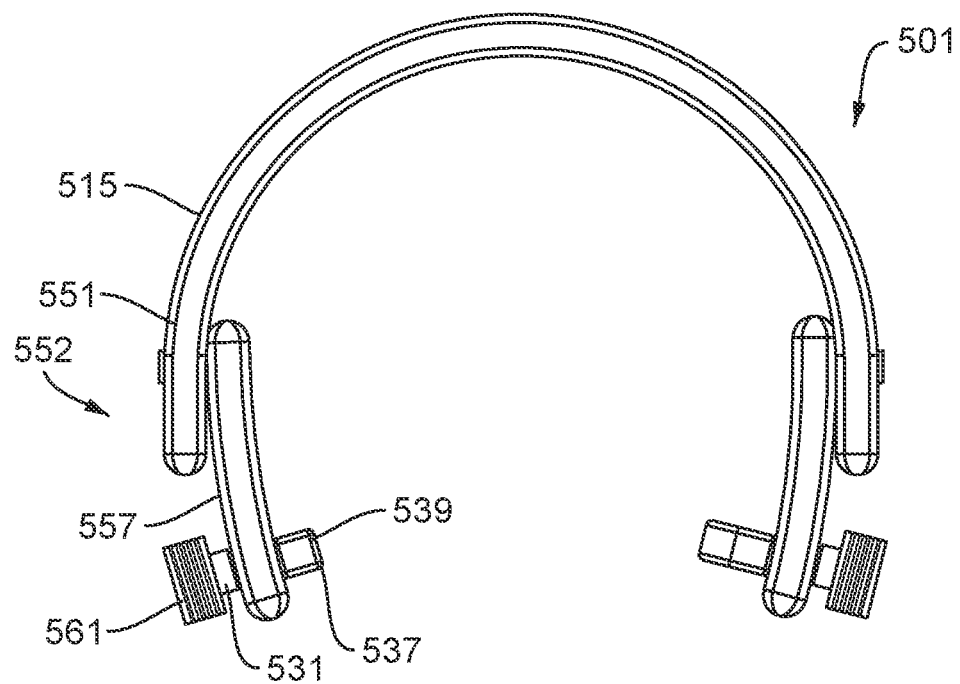
FIG. 5 shows a treatment device with screws.

FIG. 5 shows a screw-based device 501 that includes collar pressure mechanism using screws. The device 501 includes an extended collar member 515 dimensioned to extend at least partway around the neck and a projection 537 protruding inward from an inner surface of the collar member.

In the depicted embodiment, the extended collar member 515 includes a C-shaped semi-ring that extends about halfway around the neck. The semi-ring further comprises a first tang 557 fastened at a first end 552 of the semi-ring and extending therefrom. The device 501 includes a first screw 531 threaded through the first tang 557. The projection 537 comprises an elastic pad 539 disposed over an inner tip of the screw. An outer base of the screw comprises wide, grip-able head 561. Twisting the wide head 561 of the screw when the extended collar member is disposed around the neck of the patient drives the elastic pad 539 into the neck to restrict flow within the jugular vein. In the depicted embodiment, the semi-ring further comprises a second tang fastened at a second end of the semi-ring and extending therefrom, the second tang having a second screw threaded therethrough.

Figure 6:
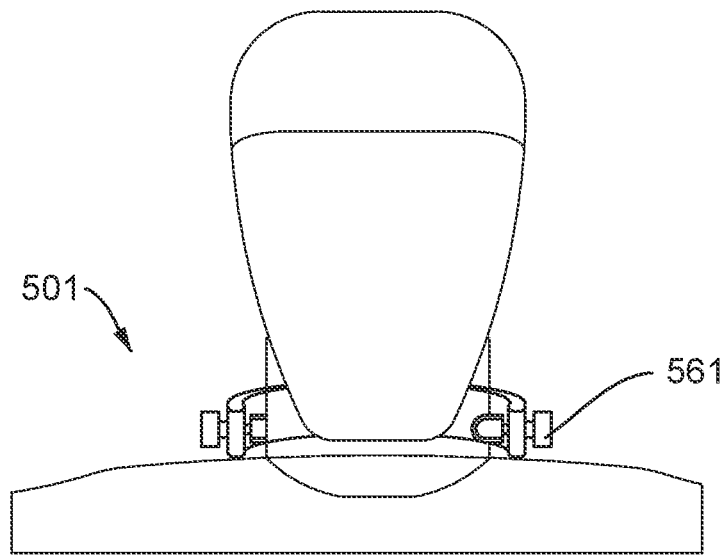
FIG. 6 shows the device with screws around the neck of a patient.

FIG. 6 shows the device 501 around the neck of a patient. FIG. 6 shows the neck collar presuming on a jugular vein (may be controlled using ultrasound). The projection 537 is positioned to press against the spot on the neck that is above a jugular vein, thereby restricting blood flow within the jugular vein.

FIG. 7 is a close-up of the device 501 for treating edema, positioned with respect to an external jugular vein 2191 and an internal jugular vein 2192. The extended collar member 515 extends at least partway around a neck of a patient. The projection 537 protrudes inward from an inner surface of the collar member. The projection 537 presses against the neck near a jugular vein. The projection 537 may be provided as a screw threaded through a portion of the collar member. Here, the projection is provided by a tip of the screw. Twisting a head of the screw when the extended collar member is disposed about the neck of the patient drives the projection into the neck to restrict flow within the jugular vein. The tip of the screw comprises an elastic pad.

FIG. 8 shows the elastic pad 539 used to restrict flow. Restricting the flow within the jugular vein causes pressure near an outlet of a lymphatic duct to decrease.

FIG. 9 depicts a patient being treated with the device 501 according to the method 401. Any suitable device 101 may be used to apply pressure that restricts flow in the vein. Other mechanisms and embodiments are within the scope of disclosure. Embodiments may include eccentric discs, inflatable balloons, inflatable collars, or other mechanisms.

Figure 10:
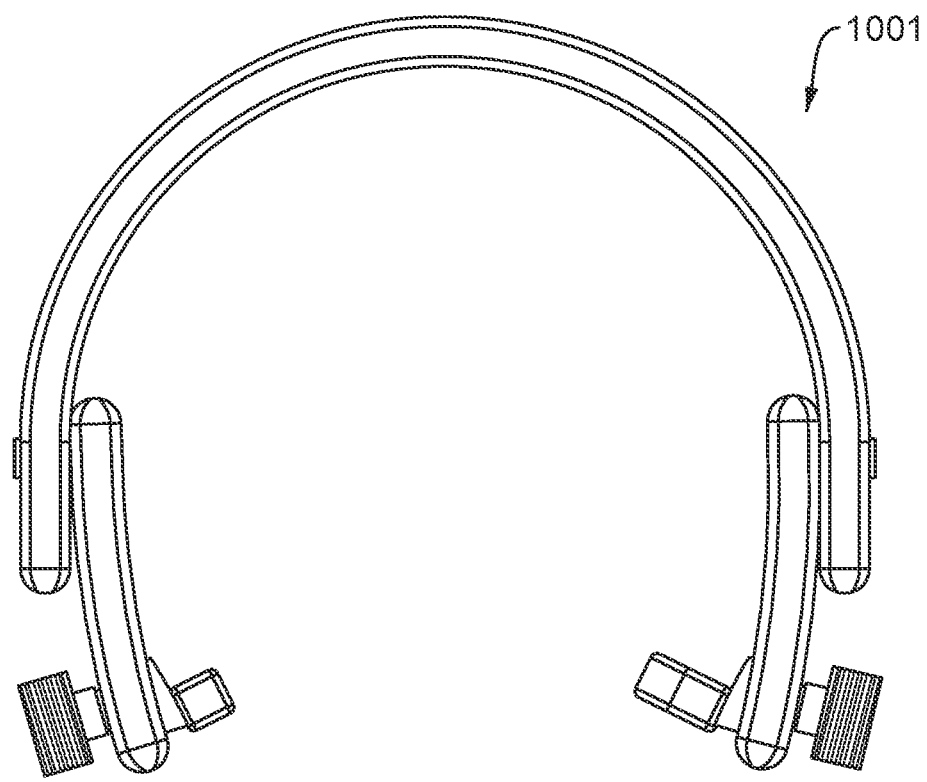
FIG. 10 shows a disc-based device.

FIG. 10 shows a disc-based device 1001 that includes collar pressure mechanism using screws and eccentric discs.

Figure 11:
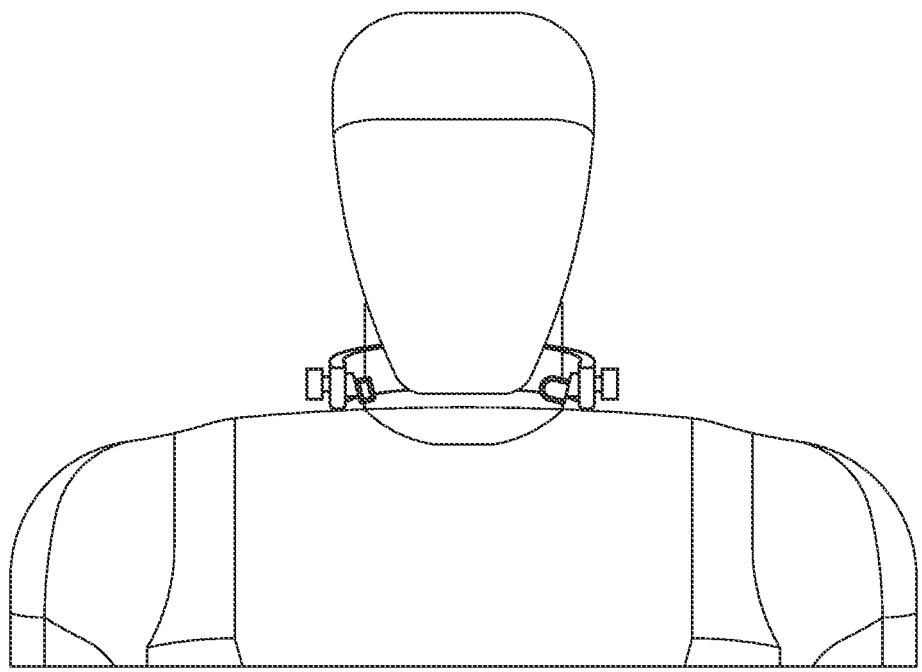
FIG. 11 shows the disc-based device on a patient.

FIG. 11 shows the disc-based device 1001 on a patient.

Figure 12:
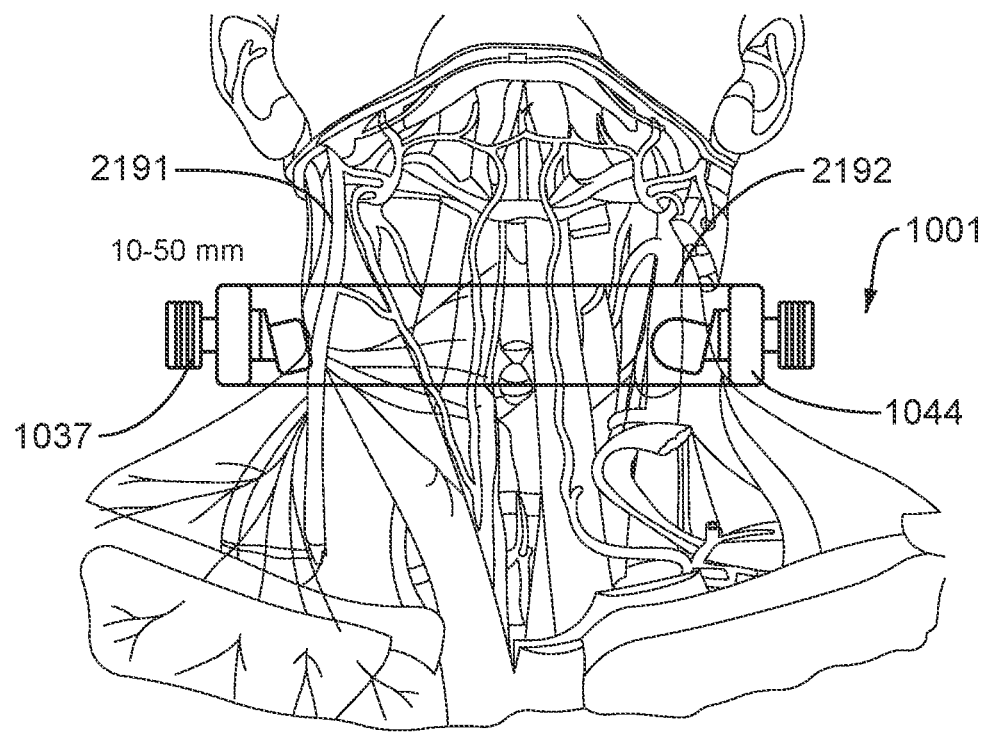
FIG. 12 is a detailed view of the disc-based device.

FIG. 12 is a detailed view of the disc-based device 1001, positioned with respect to an external jugular vein 2191 and an internal jugular vein 2192. Certain embodiments of a disc-based device 1001 include one or more screws 1037 extending through an extended collar 1044.

Figure 13:
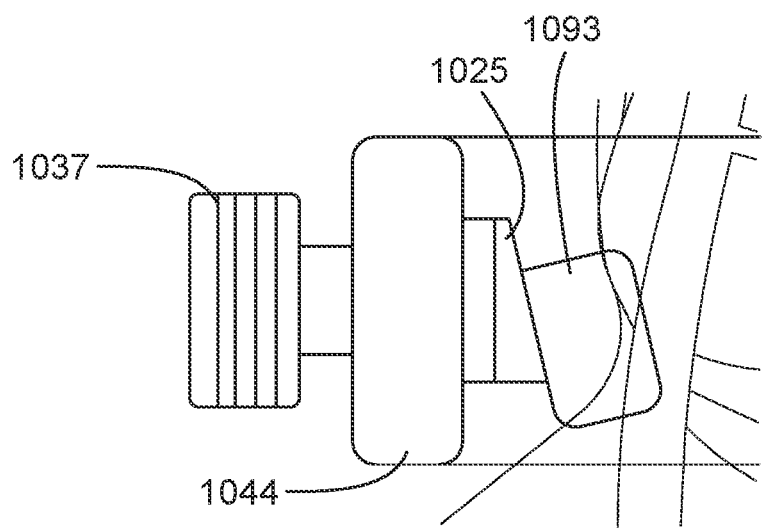
FIG. 13 is a detail view of a screw and disc of the disc-based device.

FIG. 13 is a detail view of a screw and disc of the disc-based device 1001. The screw 1037 extends through the extended collar 1044. At a tip of the screw is an asymmetric disc 1025, and a projection pad 1093 is seated on the asymmetric disc 1025. Twisting the screw 1037 drives the projection pad 1093 into a spot on the patient's neck adjacent a jugular vein, thereby restricting flow in the vein.

Other mechanisms and embodiments of the disclosure include inflatable balloons.

Figure 14:
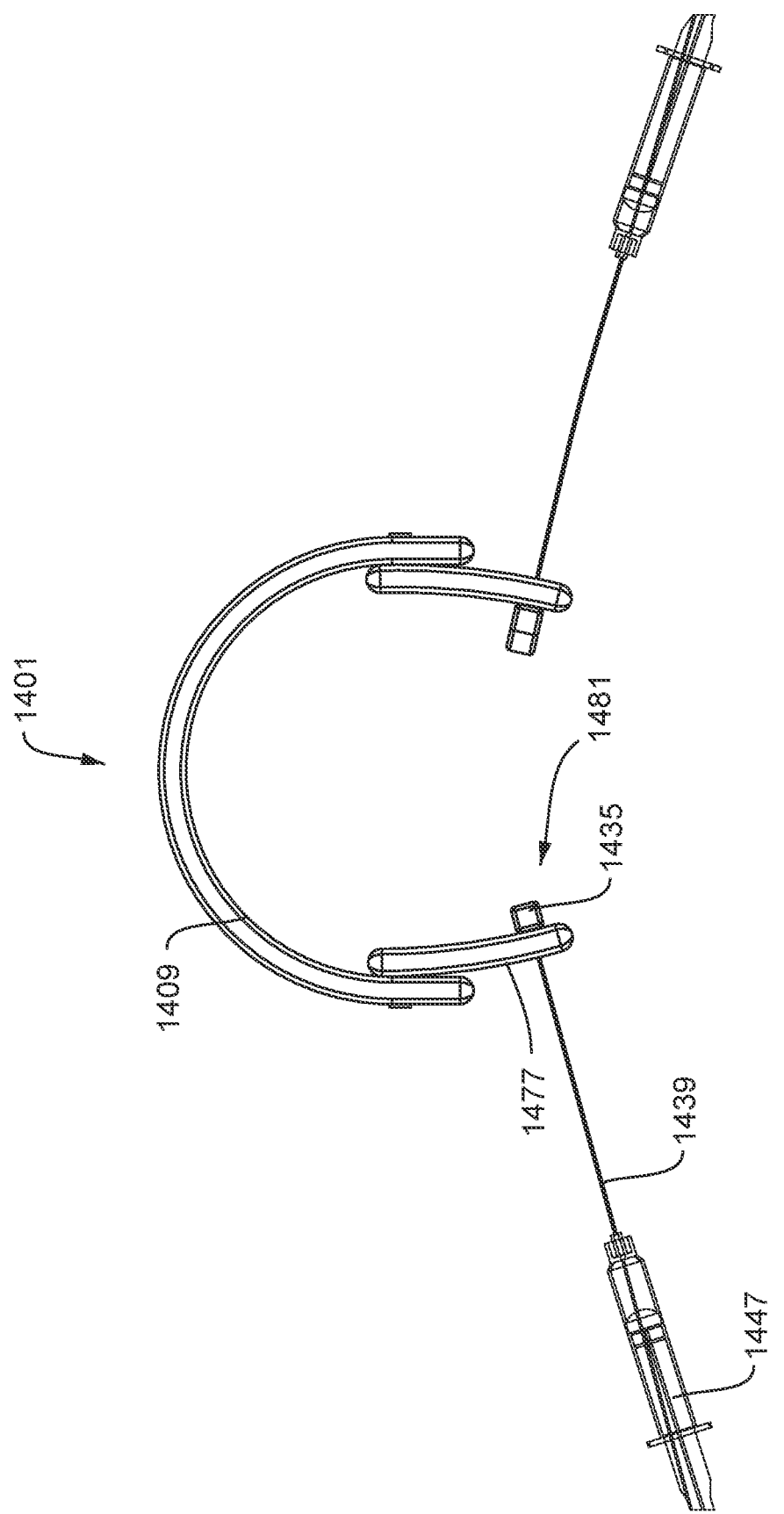
FIG. 14 shows a balloon device.

FIG. 14 shows a balloon device 1401 that includes an extended collar member comprising a rigid, C-shaped semi-ring 1409 that extends at least partially around the neck. The semi-ring 1409 comprises at least a first tang 1477 extending from a first end of the semi-ring. A projection 1437 protrudes inward from an inner surface of the first tang. Here, the projection 1437 comprises an inflatable pad 1481, fed by an inflation lumen 1439 and controlled by inflator/handle 1447. The device 1401 extends at least partway around a neck of a patient. The projection 1435 protrudes inward from an inner surface of the collar member and is positioned to press against the neck near a jugular vein, thereby restricting blood flow within the jugular vein.

Figure 15:
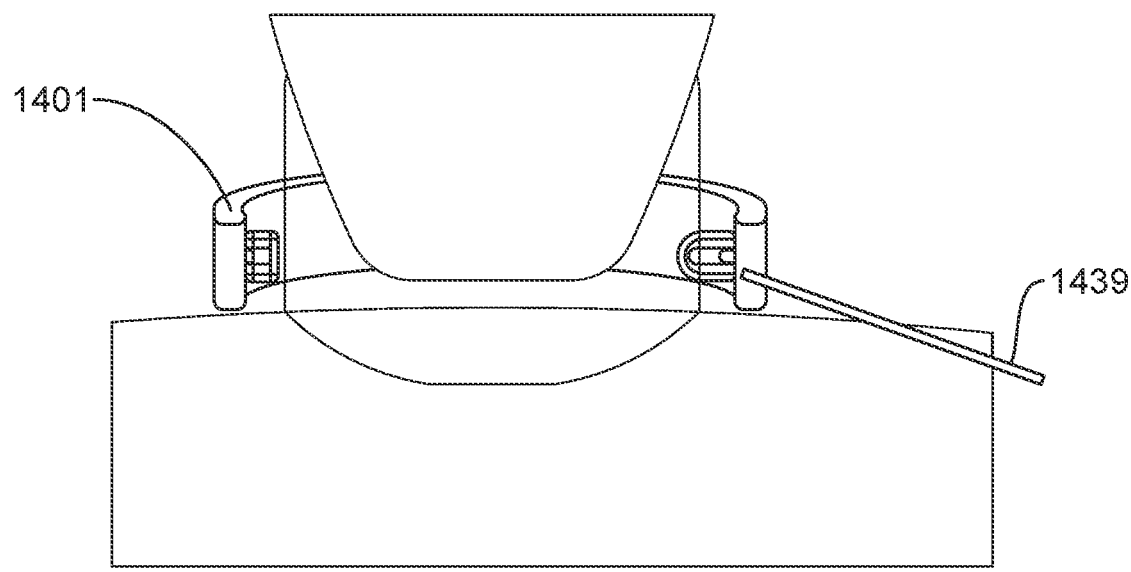
FIG. 15 shows the balloon device around the neck of a patient.

FIG. 15 shows the balloon device 1401 around the neck.

Figure 16:
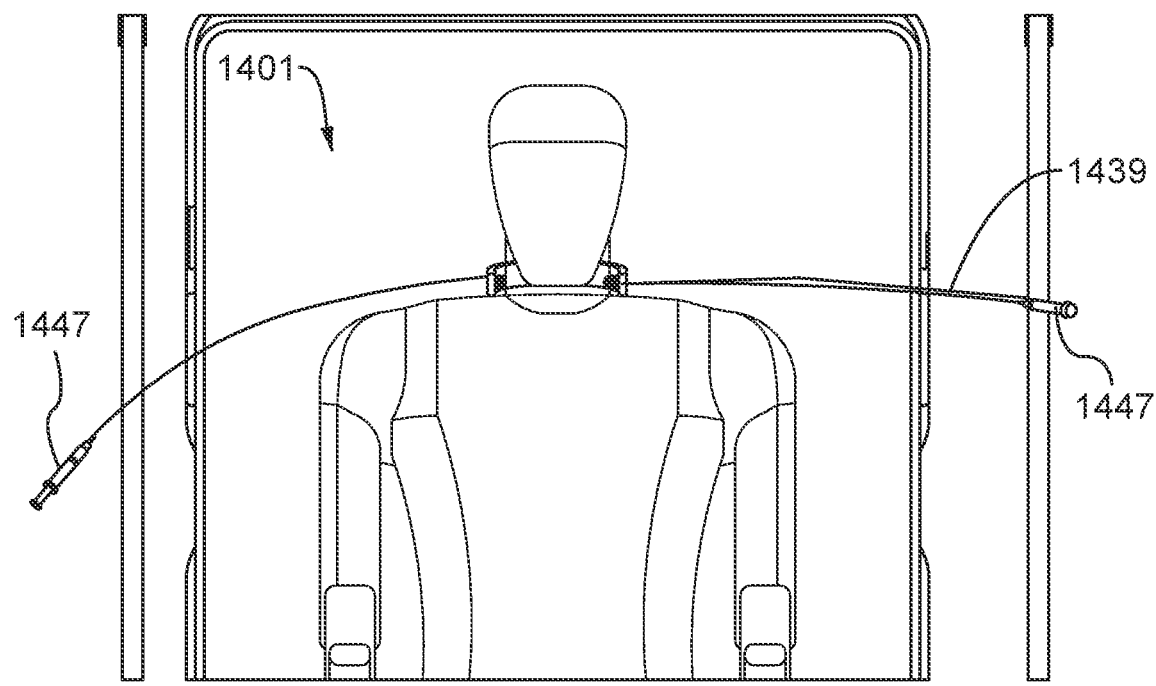
FIG. 16 shows the balloon device on the patient.

FIG. 16 shows the balloon device 1409 on the patient.

Figure 17:
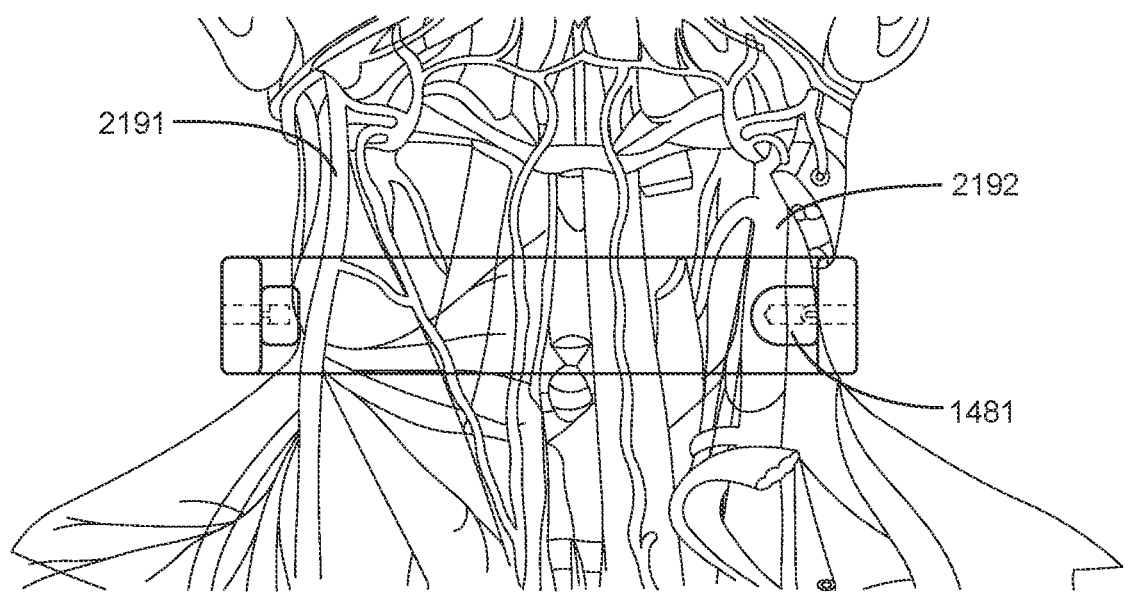
FIG. 17 is a detailed view of the balloon device.

FIG. 17 is a detailed view of the balloon device 1409, positioned with respect to an external jugular vein 2191 and an internal jugular vein 2192.

Figure 18:
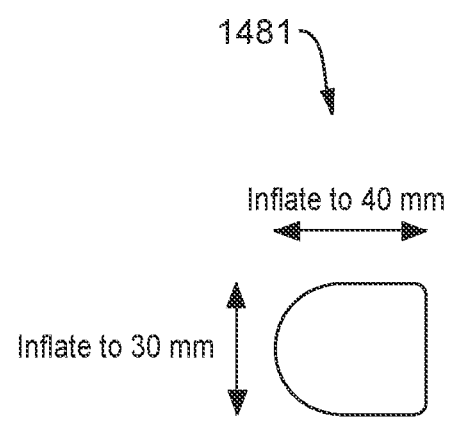
FIG. 18 shows an inflatable pad.

FIG. 18 shows the inflatable pad 1481. As shown (e.g., in FIG. 14) the projection 1435 includes an inflatable pad 1481. Inflating the pad 1481 when the extended collar member is disposed around the neck of the patient drives the pad into the neck to restrict flow within the jugular vein. In other embodiments all or portions of collar or neck cuff are themselves inflatable.

Figure 19:
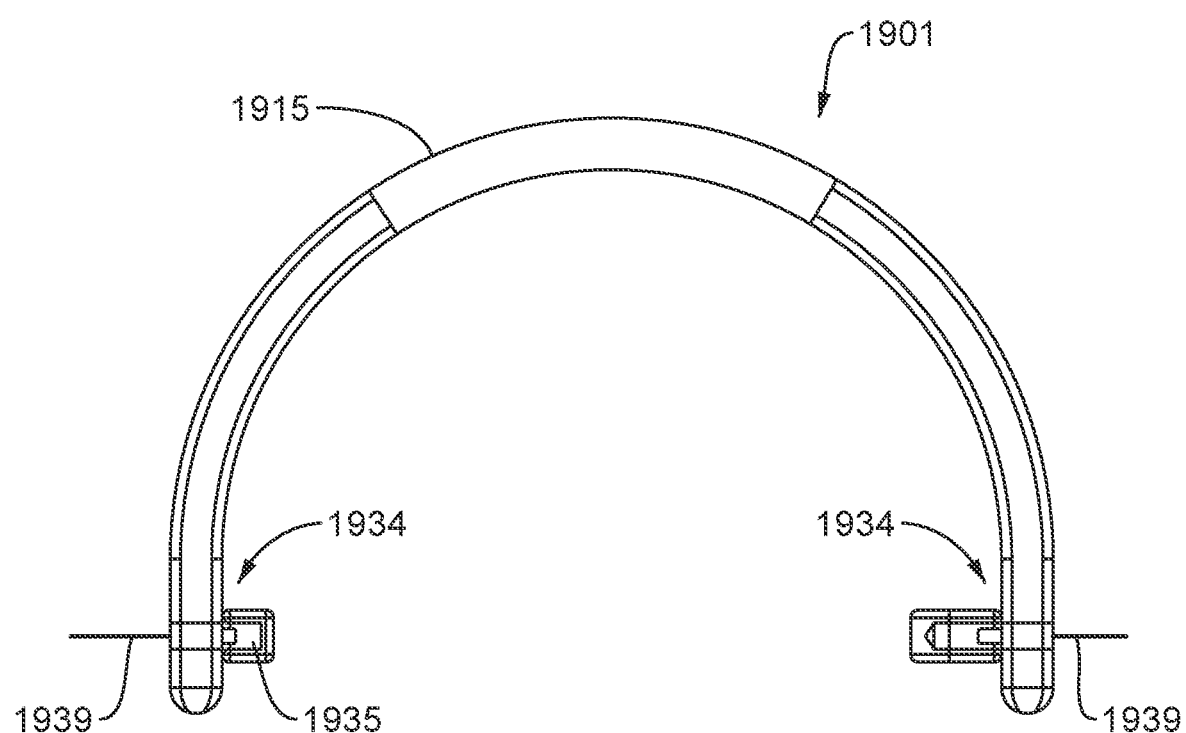
FIG. 19 shows an inflatable collar device.

FIG. 19 shows an inflatable collar 1901 in which a collar pressure mechanism uses an collar member 1915 with elastic biocompatible pads 1935 on inflatable portions 1934 of the collar. One or more inflation lumens 1939 are in fluid communication with the inflatable portions 1934 and one or more inflation mechanisms (not shown). The inflatable collar device 1901 for treating edema includes an extended collar member 1915 dimensioned to extend at least partway around a neck of a patient. A projection 1935 protrudes inward from an inner surface of the collar member 1915. The projection 1935 may be positioned by a physician to press against the neck near a jugular vein.

Figure 20:
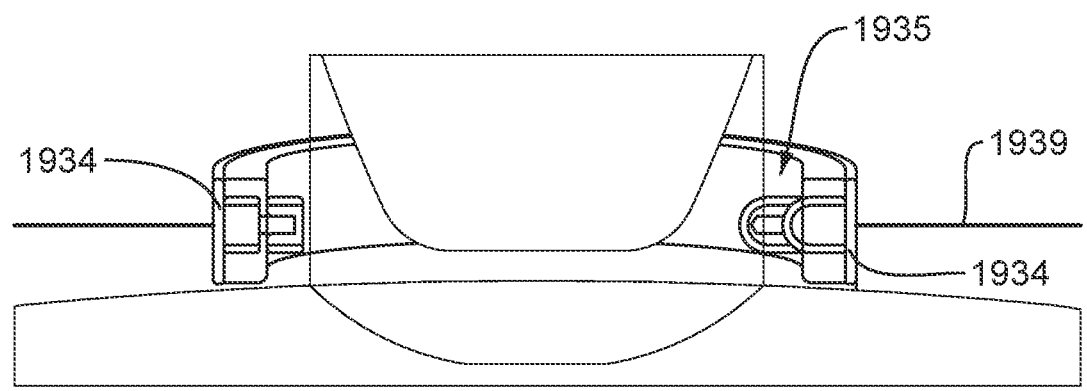
FIG. 20 shows the inflatable collar device on a patient.

FIG. 20 shows the inflatable collar 1901 disposed about the neck. Inflating the portions 19354 when the collar member is disposed around the neck of the patient drives the projection 1935 into the neck to restrict flow within the jugular vein.

Figure 21:
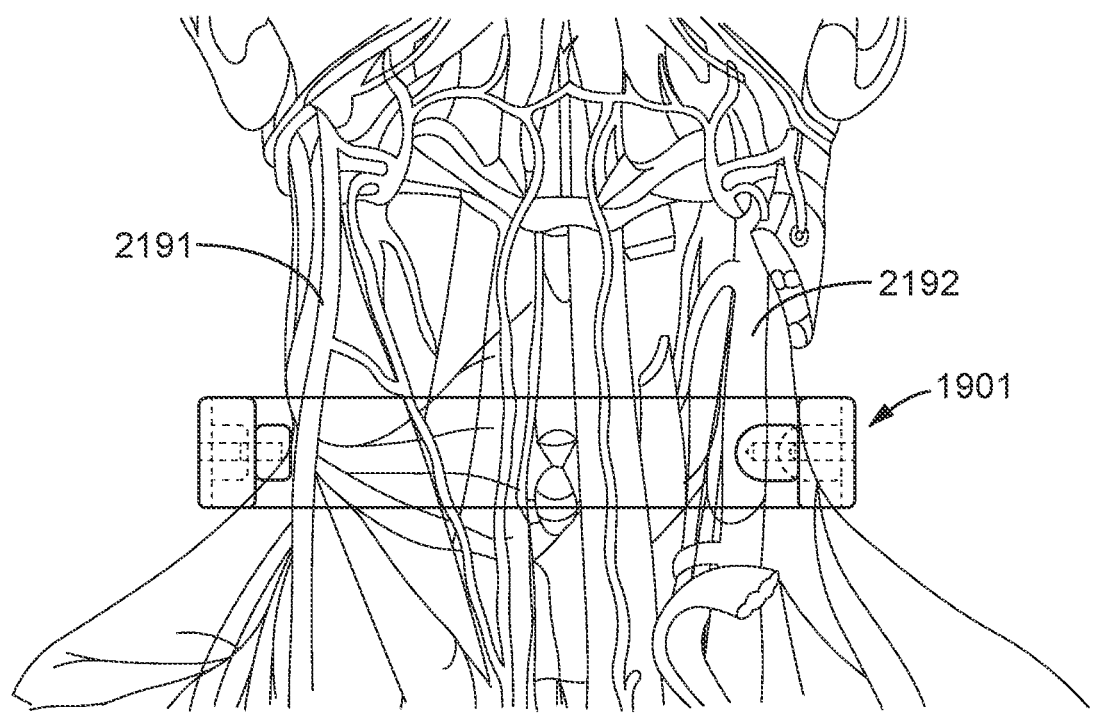
FIG. 21 shows positioning for the inflatable collar device.

FIG. 21 shows positioning for the inflatable collar 1901. The dotted lines show the positions of the projections 1935 when the collar 1901 is not inflated. When the collar 1901 is inflated, the projections 1935 a driven into the skin, to the positions shown by the solid lines. Also depicted are locations of the external jugular vein 2191 and an internal jugular vein 2192

Figure 22:
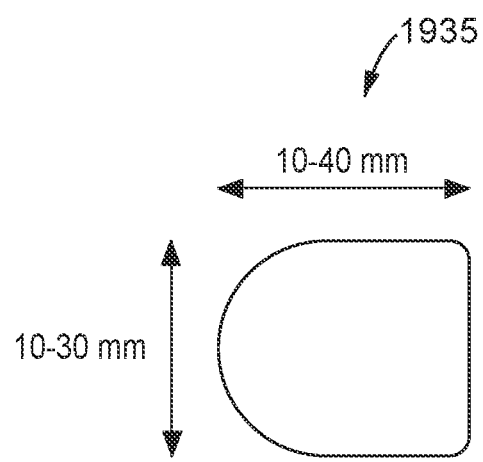
FIG. 22 shows a projection member of the inflatable collar device.

FIG. 22 shows the projection 1935.

In other embodiments, the disclosure provides a device for treating edema in which an extended collar member extends at least partway around a neck of a patient and presses a projection against the neck near a jugular vein and in which the collar member self-fastens or is enclosed in a cuff that self-fastens.

Figure 23:
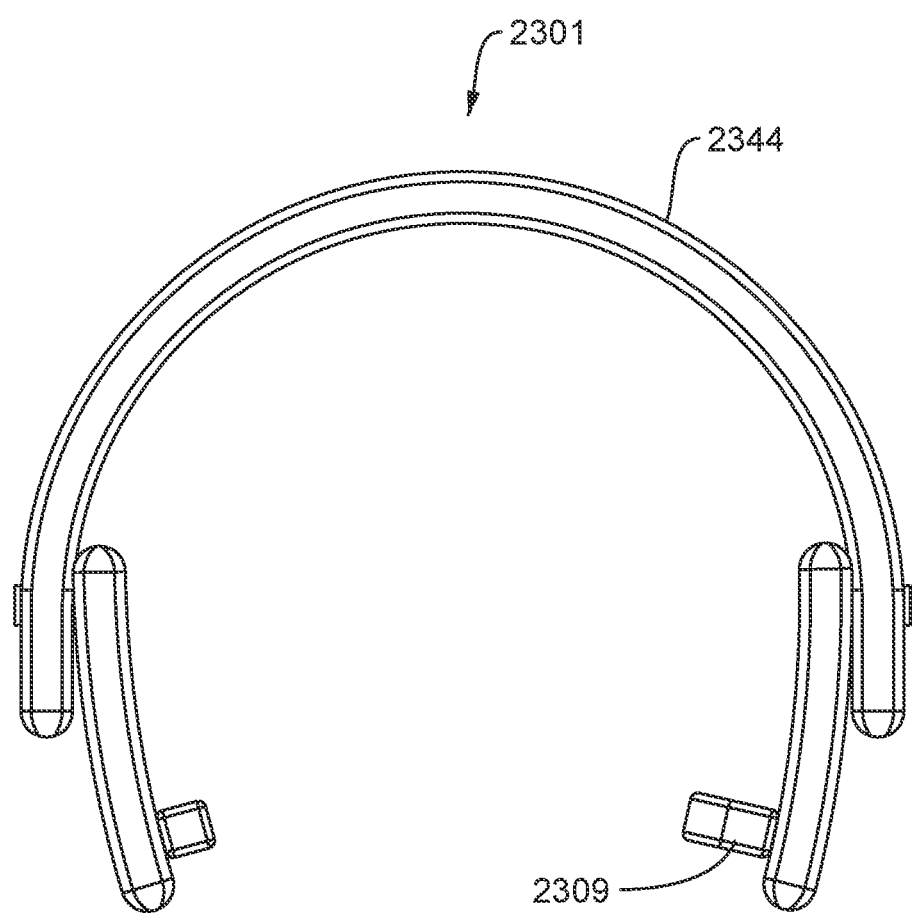
FIG. 23 shows a tightening cuff style fastening device.

FIG. 23 shows a tightening cuff style fastening device 2301 in which a collar pressure mechanism uses a pressure tightening mechanism. The device 2301 includes an extended member 2344 that positions one or more projections 2309 at a spot on a neck of a patient adjacent a jugular vein.

Figure 24:
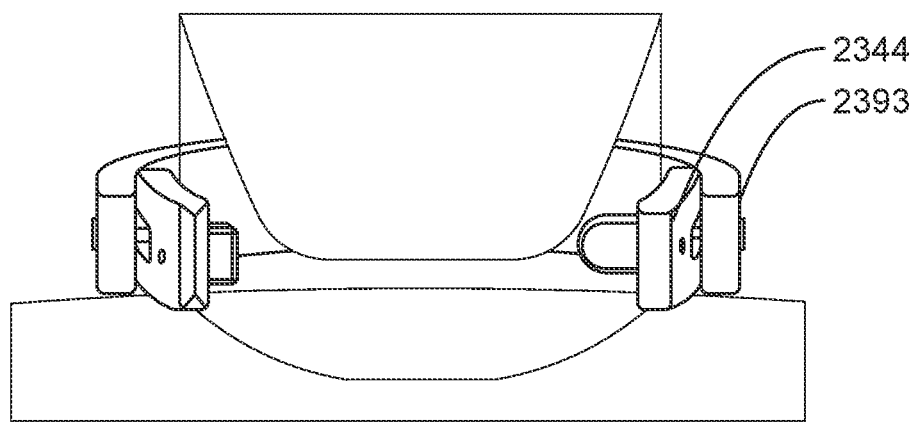
FIG. 24 shows the tightening cuff style device in place.

FIG. 24 shows the device 2301 in place, with the extended member 2344 being substantially covered by tightening cuff 2392. The tightening cuff 2393 can be squeezed tight through a series of clicks, e.g., due to a plastic detente mechanisms along a strap that slides through a receiver with a ratchet prong. Thus the extended member 2344 is provided with the tightening cuff 2392, which has a releasable fastening mechanism defining a plurality of stops corresponding to progressively tighter fittings, such that cinching the extended collar mechanism closed drives the projection into the neck to restrict flow within the jugular vein. The tightening cuff device 2301 may be tightened by any suitable mechanism including, for example, a slider and clicker, a plunger and ladder, male to female connectors, a cable tie-style fastener, a latch, and electronic sliding device, which may be controlled or not by a controller.

Figure 25:
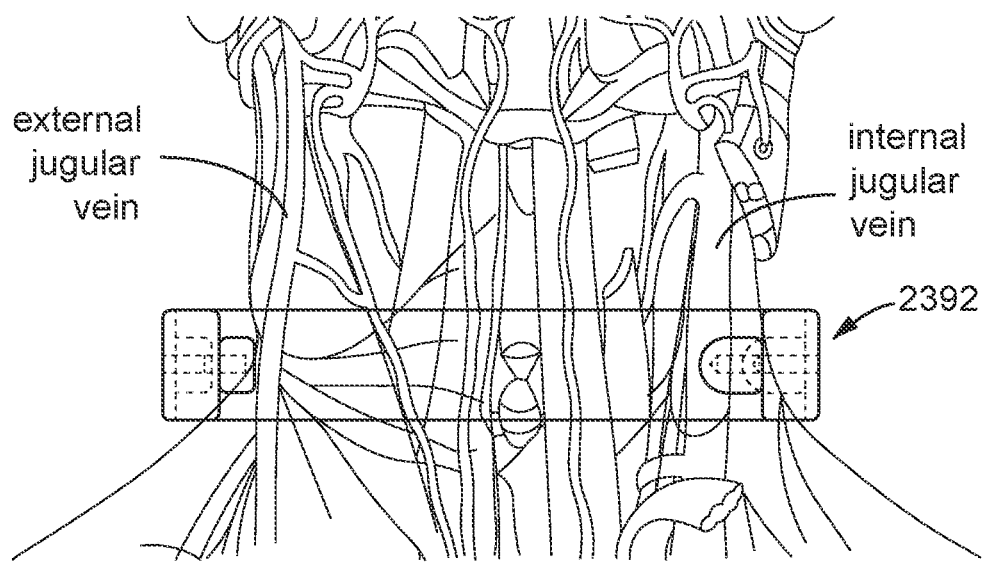
FIG. 25 shows a tightening-cuff on a patient

FIG. 25 shows the tightening-cuff 2392 in place on a patient. The tightening of the tightening cuff 2392 creates a restriction in a vein such as the internal jugular vein.

Figure 26:
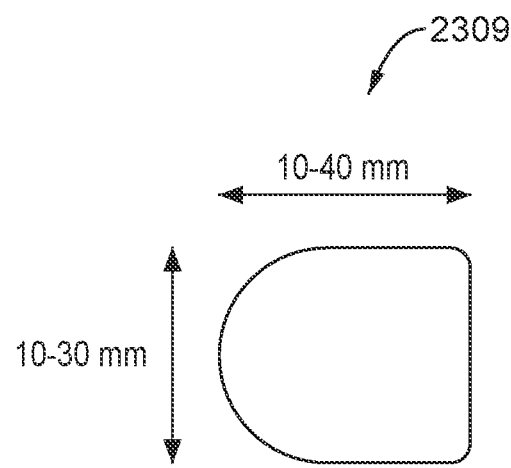
FIG. 26 shows a projection included in the tightening cuff style device.

FIG. 26 shows a projection 2309 included in the tightening cuff style fastening device 2301. Other embodiments are within the scope of the disclosure.

Figure 27:
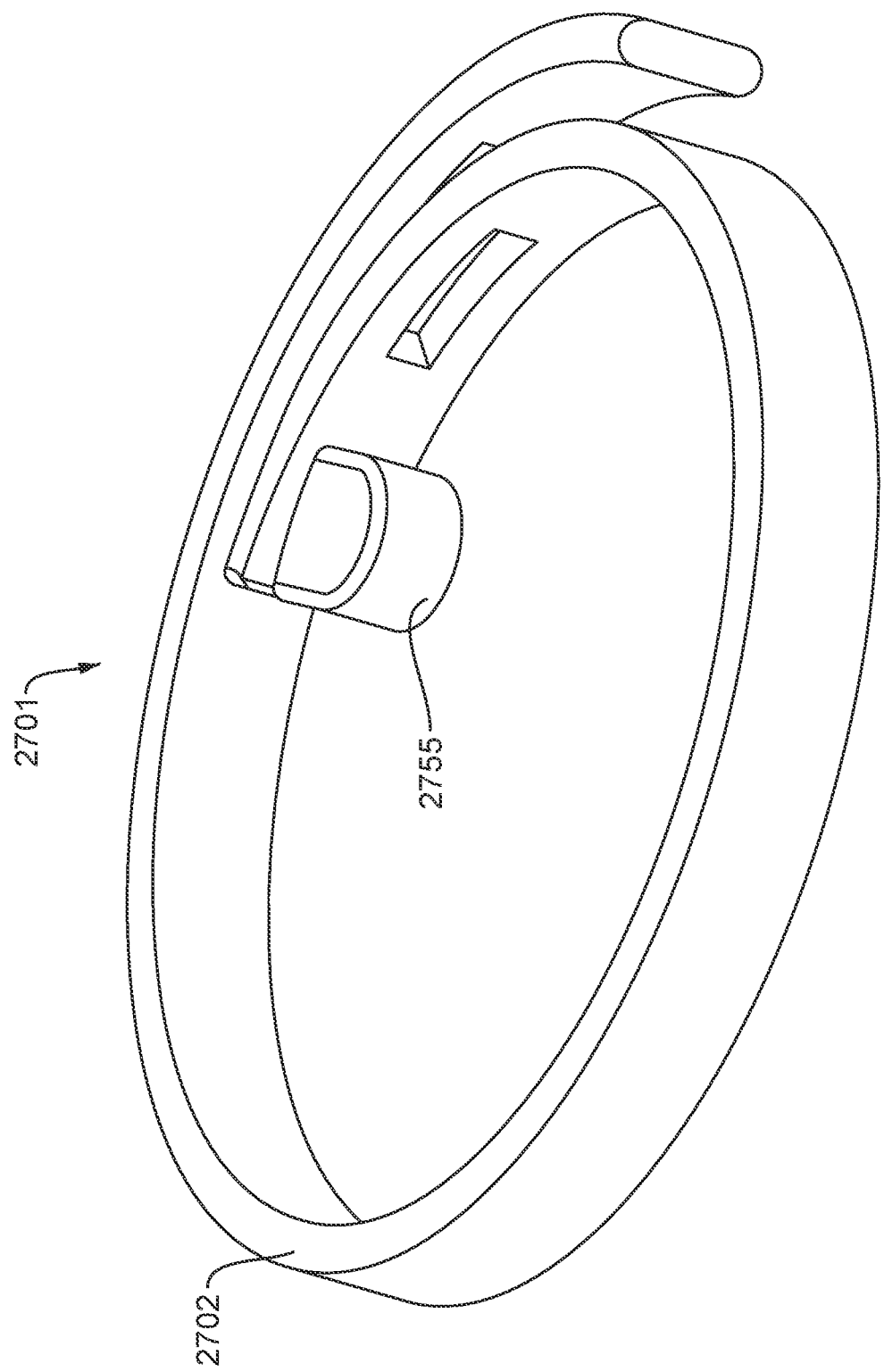
FIG. 27 shows a limb-cuff device for reducing the CVP.

FIG. 27 shows a limb-cuff device 2701 for reducing the CVP by restricting externally one or both of the femoral veins. The limb-cuff device 2701 includes an extended, closeable strap 2702 with at least one projection 2755 protruding therefrom.

FIG. 28 shows a patient with the limb-cuff device 1701.

FIG. 29 shows the limb cuff device 2701 disposed with respect to a femoral vein 3991, as well as a long saphenous vein 3992 and tributaries 3663 of long saphenous vein.

Figure 30:
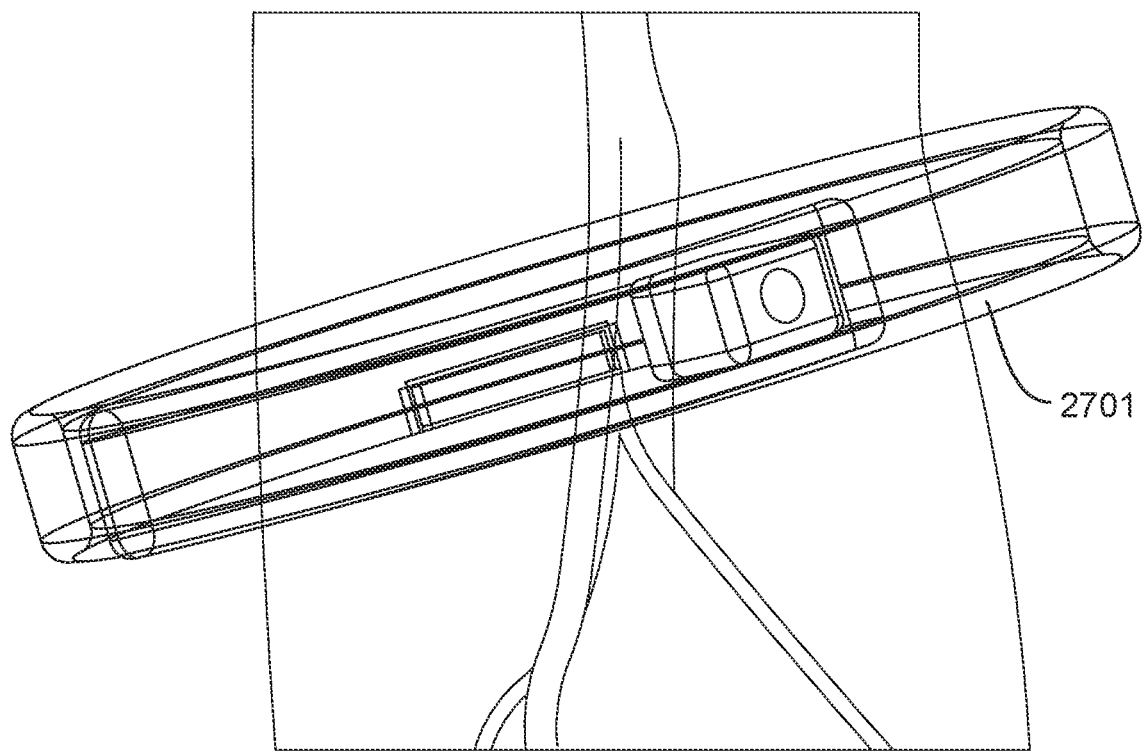
FIG. 30 is a close-up of the limb cuff device on a patient.

FIG. 30 is a close-up of the limb cuff device 2701 on a patient. The limb cuff device 2701 operates as an external adjustable cuff for partially or fully restricting the jugular or femoral vein. The limb cuff device 2701 may operate by pressing on a femoral vein and may be controlled by ultrasound. The limb cuff device 2701 may fit to the left or right femoral vein. The limb cuff device 2701 may be tightened by any suitable mechanism such as screws, scotch bundling wrap, rotating an eccentric disk, pressure pad inflation, leg device inflation (i.e., inflate the limb cuff device 2701), slider and clicker, plunger and ladder, male to female connectors, a cable tie, a latch, or an electronic sliding device (controlled or not by a controller).

Figure 31:
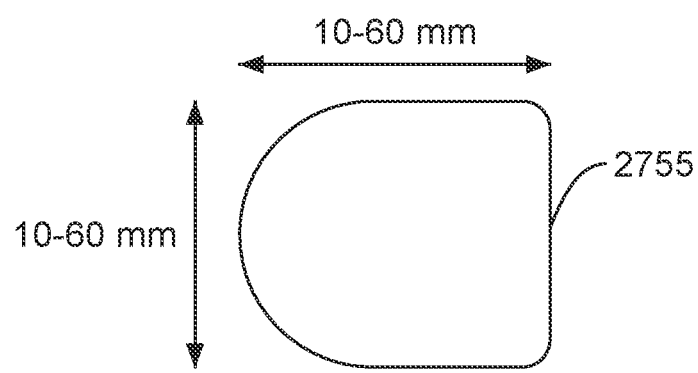
FIG. 31 shows a projection member included on an inner surface of the limb cuff device.

FIG. 31 shows a projection 2755 for the limb cuff device 2701. The projection 2755 may be an elastic pad. Other embodiments are within the scope of the disclosure.

Figure 32:
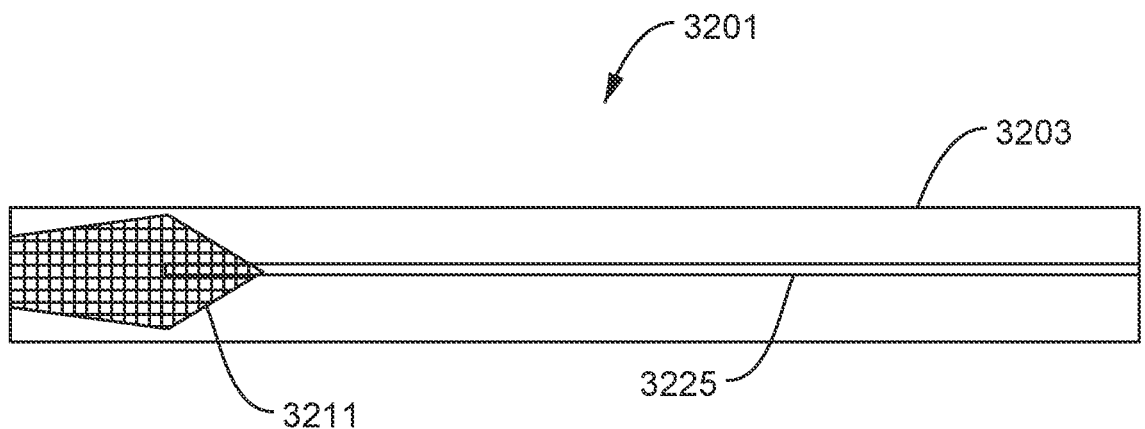
FIG. 32 shows a deployable stent device.

FIG. 32 shows a deployable stent device 3201 for treating edema. The a deployable stent device 3201 is shown in an un-deployed configuration. A collapsed basket stent 3211 is contained within a catheter 3203 attached to a distal portion of a pushable wire 3225. When the catheter 3203 is retracted relative to the pushable wire 3224, a shape-memory material of the basket stent 3211 causes the basket stent to assume a deployed configuration.

Figure 33:
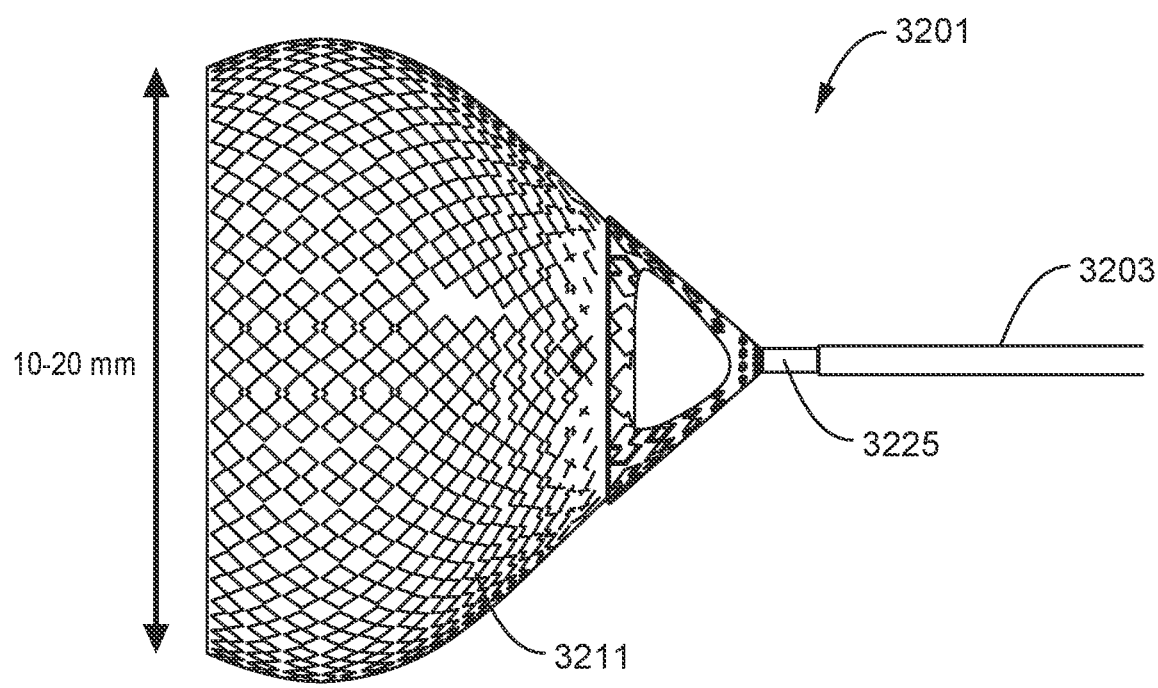
FIG. 33 shows the deployable stent device in a deployed configuration.

FIG. 33 shows the deployable stent device 3201 in a deployed configuration. The deployable stent device 3201 provides a device for reducing pressure by restricting the vein internally using a Nitinol stent graft with an adjustable restrictor to the flow through it. In some embodiments, the basket stent 3211 does not have an un-deployed configuration as shown in FIG. 32, but instead is fully expanded, and sliding the catheter 3203 with respect to the pushable wire 3225 deforms the basket stent 3211 adjusting a porosity therethrough.

As an example of an intravenous flow restrictor, a catheter can be inserted via a central line placement technique and advanced a few cm into the vein. A partial restriction can be performed using a balloon that opposes the vein and leaves an internal pathway for the blood.

Another indwelling intravenous apparatus can be a balloon and a shaft with longitudinal openings that can be adjusted relative to an introducer sheath and thus control the flow through the restrictor.

Figure 34:
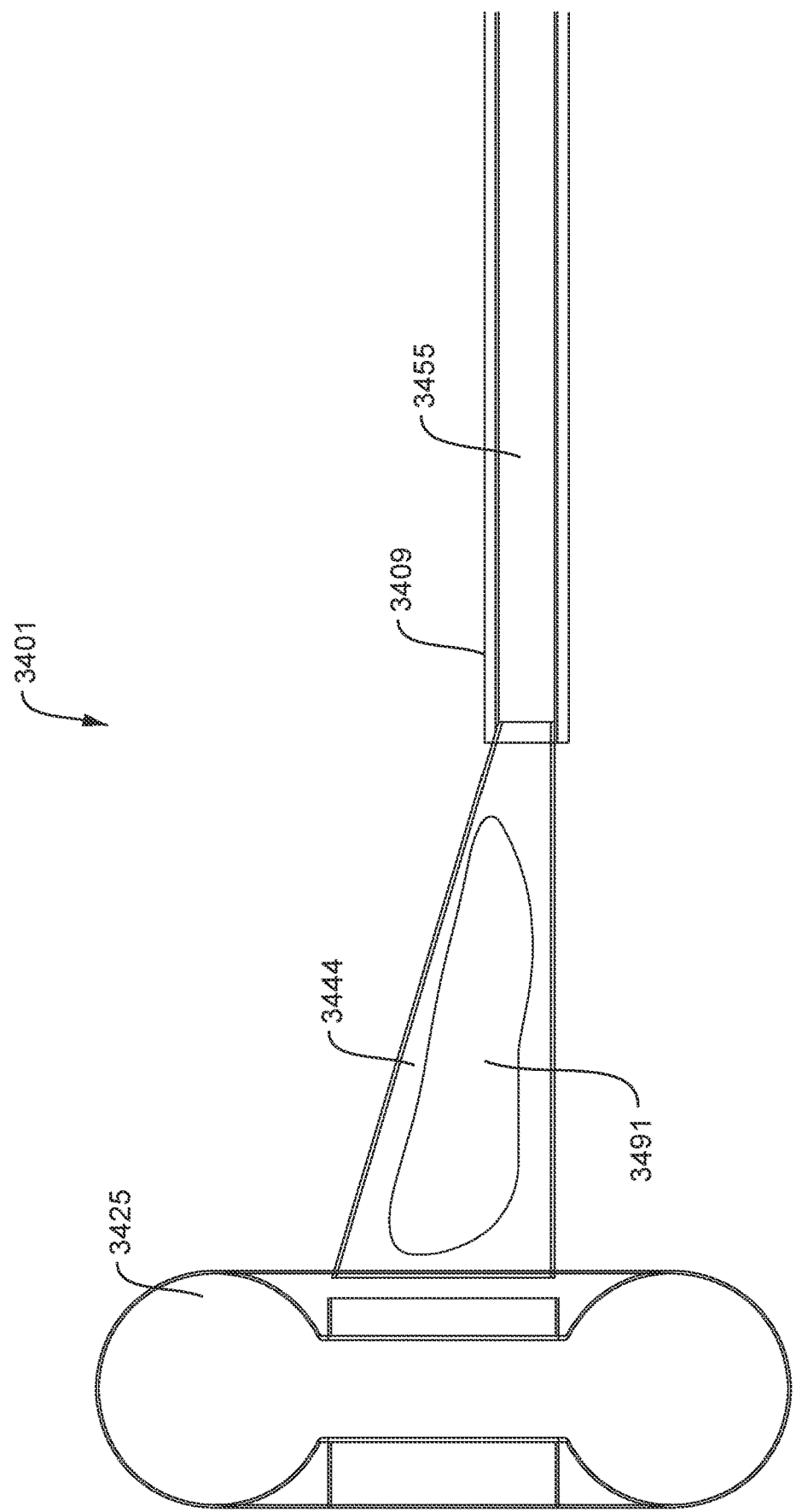
FIG. 34 shows an open-sheath device for treating edema.

FIG. 34 shows an open-sheath device 3401 for treating edema. The open-sheath device 3401 includes a balloon 3425 and a shaft, or sheath 3444, with longitudinal openings 3491 that can be adjusted relative to an introducer catheter 3409 and thus control the flow through the restrictor. The catheter 3409 preferably includes an inflation lumen 3455 allowing a user to expand the balloon 3425 and control the open-ness of the openings 3491, thereby controlling flow through the open-sheath device 3401. In methods of the disclosure, the open-sheath device 3401 is introduced into a blood vessel of a patient, preferably a jugular vein. The open-sheath device 3401 is navigated so that it is near an outlet of a lymphatic duct. The balloon 3425 is inflated and the sheath 3444 restricts flow, thereby creating a low-pressure zone near the outlet of lymphatic duct. This causes lymph to drain from the lymphatic system to the circulatory system, thereby relieving edema.

Device and methods of the disclosure may use other features and configurations. On devices such as the open-sheath device 3401, one or more pressure sensor distally and/or proximally to the balloon 3425 can be used to regulate the pressure in the part of the vein that extends from the balloon to the right atrium. Typically, the pressure range that would be desired to achieve is 0-5 mm Hg but lower pressures down to −5 mm Hg may be favorable. The restriction can be done for long duration of several days to enable edema fluid removal. The restriction can be left indwelling or externally deployed for longer durations of weeks and months and deployed a few hours each day to prevent ADHF episodes from occurring.

Other embodiments are within the scope of the disclosure.

Figure 35:
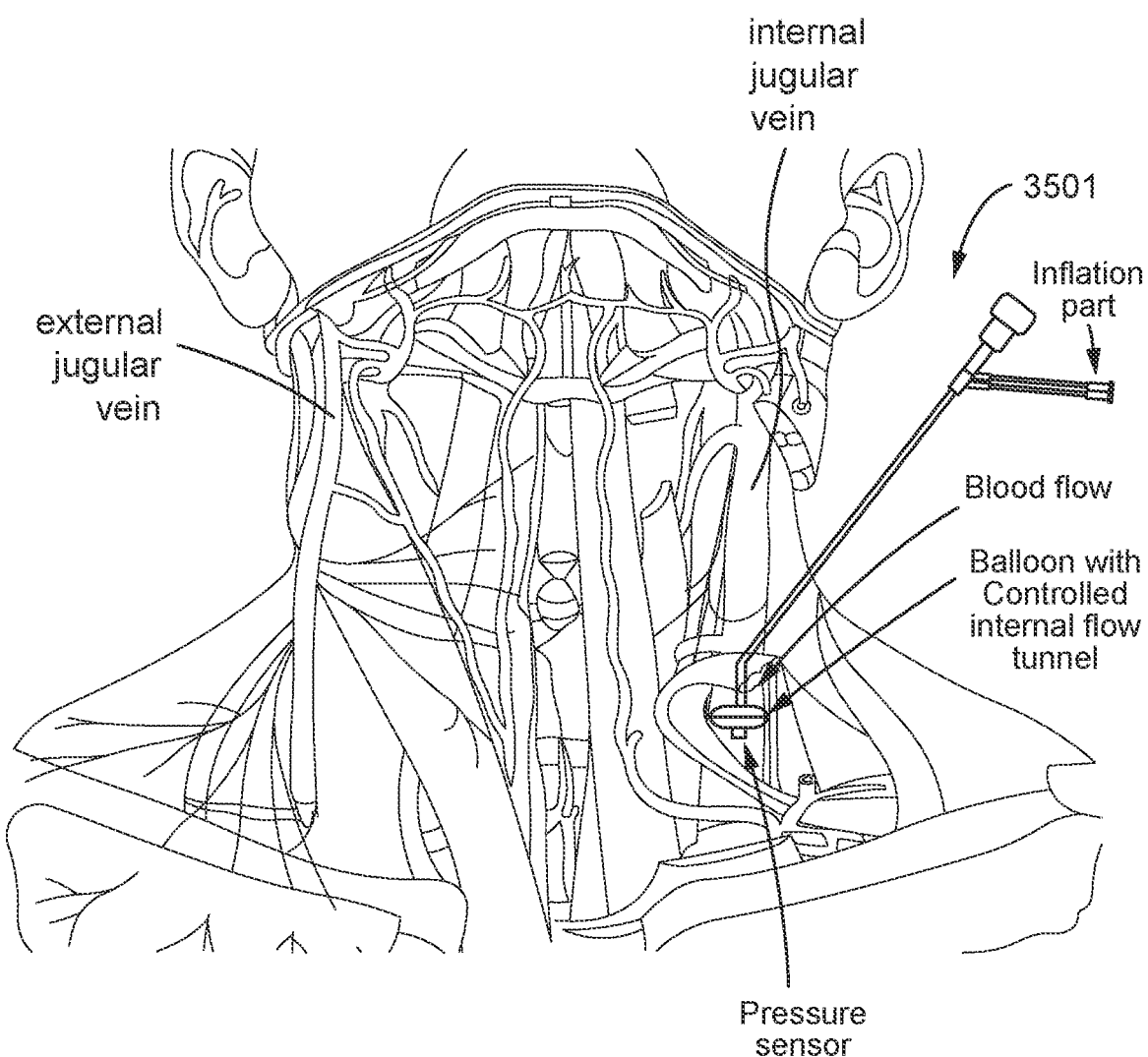
FIG. 35 shows the restriction device in a jugular vein.

FIGS. 35-44 show an intravascular restriction device 3501 that uses an internal balloon with a restrictor to fully or partially restricting a vein FIG. 35 shows the restriction device 3501 in a jugular vein of a patient.

Figure 36:
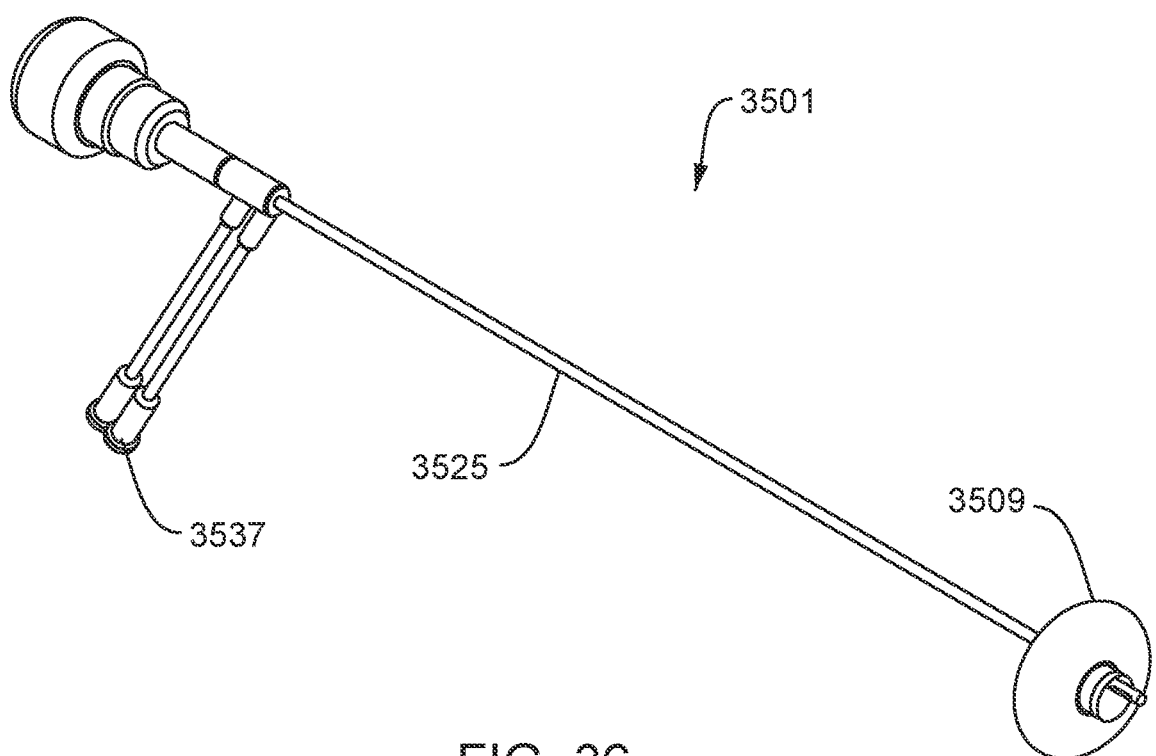
FIG. 36 shows the restriction device.

FIG. 36 shows the restriction device 3501, useful for reducing pressure by restricting the vein internally using a balloon with an adjustable restrictor to the flow through it. The restriction device 3501 preferably includes an extended catheter shaft 3525 with a balloon 3509 on a distal portion. An inflation port 3537 may be provided to inflate the balloon 3509.

Figure 37:
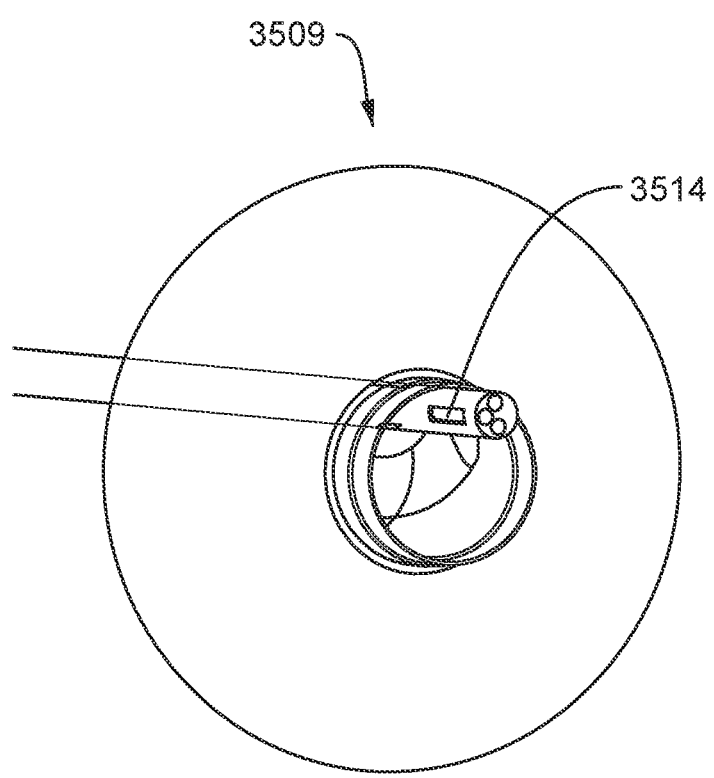
FIG. 37 is a close-up of the balloon of the restriction

FIG. 37 is a close-up of the balloon 3509 of the restriction device 3501. The device 3501 optionally includes a pressure-sensing mechanism 3514 such as a pressure-sensing lumen or mechanical pressure sensor.

Figure 38:
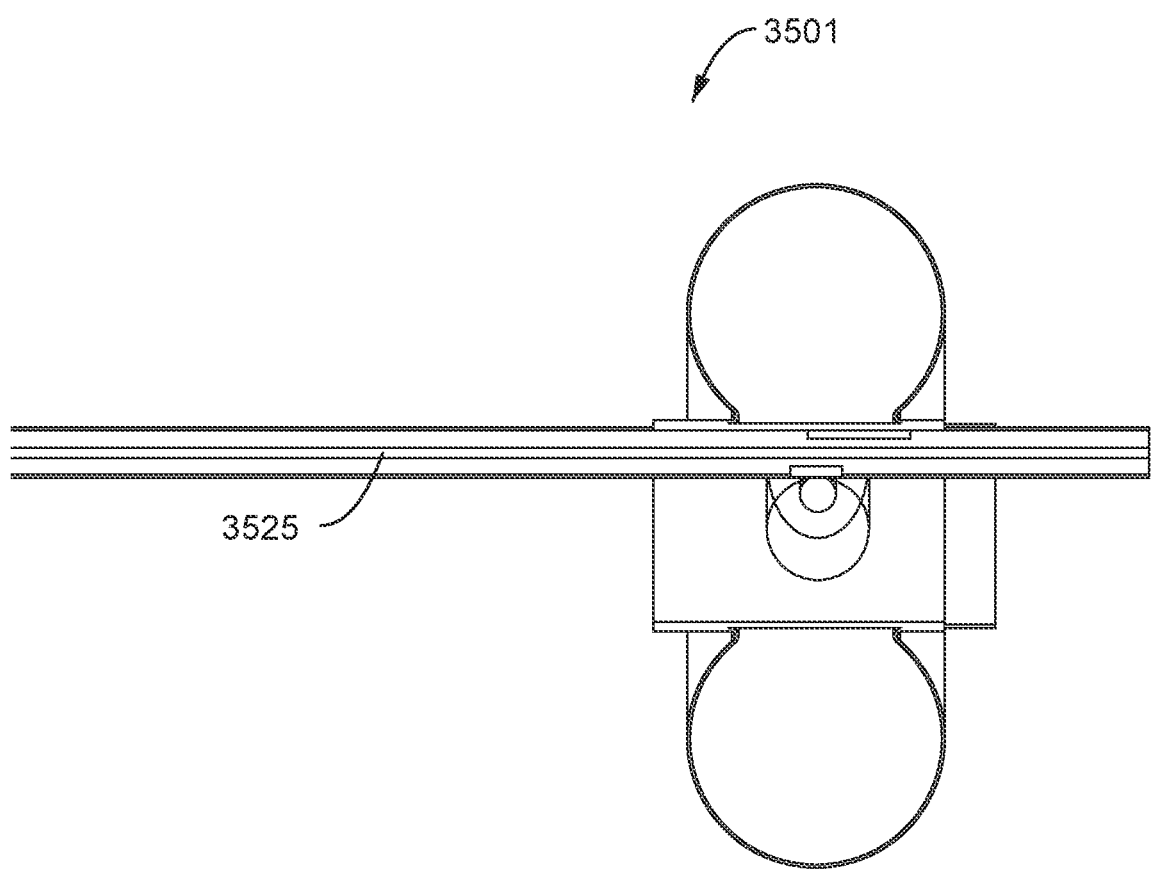
FIG. 38 is a cross section along and through the restriction device.

FIG. 38 is a cross section through the restriction device 3501.

Figure 39:
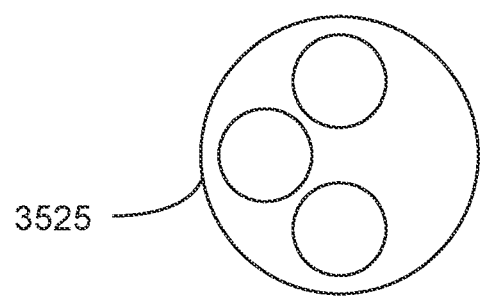
FIG. 39 is a cross-section across the catheter shaft of the restriction device.

FIG. 39 is a cross-section across the catheter shaft 3525 of the restriction device 3501.

Figure 40:
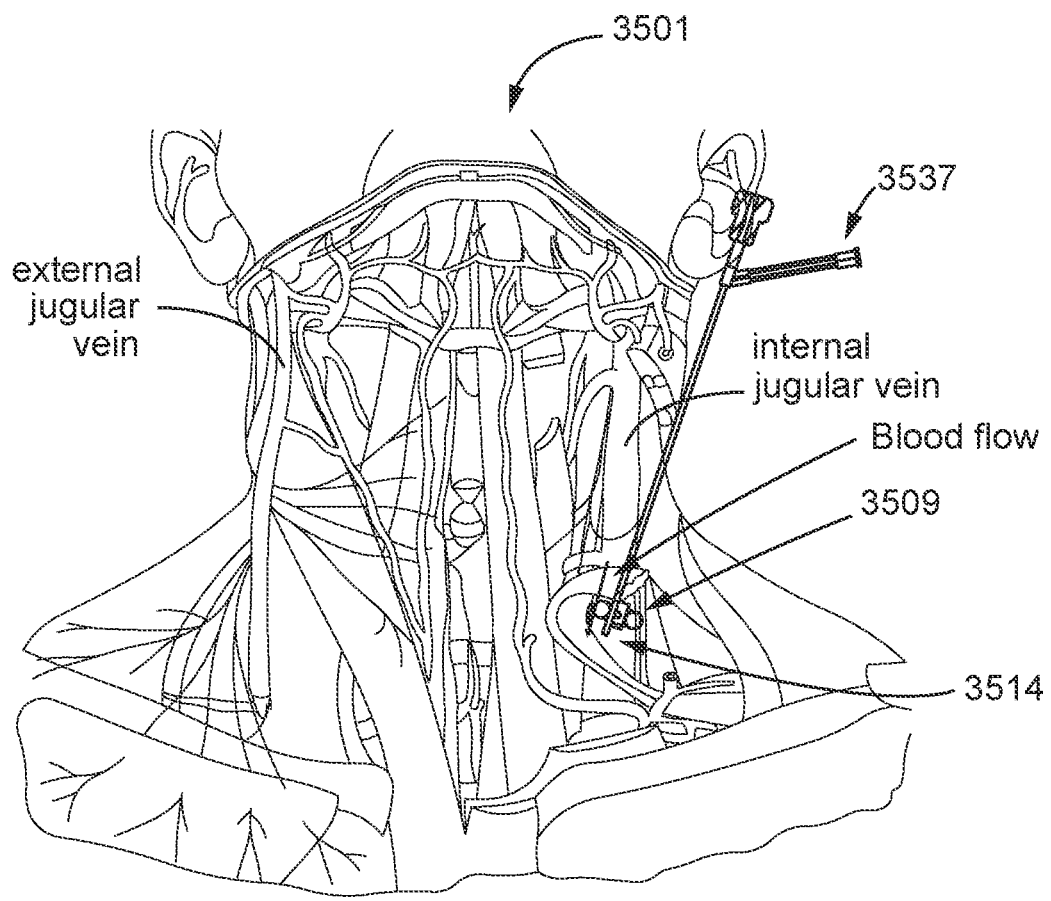
FIG. 40 shows the restriction device in vasculature of a patient.

FIG. 40 shows the restriction device 3501 in vasculature of a patient. A pressure sensor may be located on the device 3501. Blood flows through the device, and inflation of the balloon modulates a diameter of an internal flow tunnel defined through the balloon, thereby controlling flow.

Figure 41:
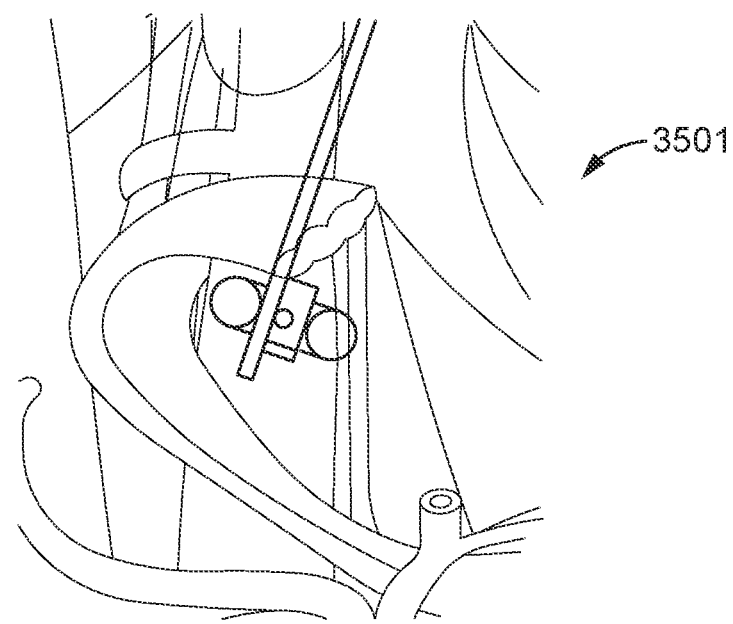
FIG. 41 is a close up of the restriction device in the patient.

FIG. 41 is a close up of the restriction device 3501 in the vasculature of the patient. Other embodiments are within the scope of the disclosure.

FIG. 42 depicts a collapsible tube device 4201 for treating edema. The collapsible tube device 4201 includes a catheter 4211 carrying a balloon 4215 connected to a collapsible tube 4219. A distal portion 4225 of the catheter 4211 has a tip 4227. The collapsible tube device 4201 may be used as a self-regulating flow restrictor comprised of a catheter 4211 with hollow balloon 4215 which is attached to a collapsible tube 4219.

FIG. 43 shows the balloon 4215 of the collapsible tube device 4201.

FIG. 44 shows the collapsible tube device 4201 located within a vessel 4401 of a patient. The catheter tip 4227 is directed toward the heart.

As shown, P2 is the central venous pressure (CVP) near the heart. The central venous pressure is known to be pulsatile due to heart valves function and respirations. P3 is the pressure within the collapsible tube and P1 is the upstream blood pressure. When P3<P2 the tube collapses and prevents flow.

Looking at FIG. 44, note that the balloon 4215 prevents flow in an outer portion of the vessel 4401. Thus, any blood flowing through the vessel 4401 must flow through the collapsible tube 4219. A cross-sectional area of the collapsible tube 4219 is smaller than a cross-sectional area of the blood vessel 4401.

As the collapsible tube 4219 has smaller cross section than the vessel 4401, and due to mass conservation, the flow velocity in the collapsible tube 4219 is higher than the flow velocity in the vein 4401. Therefore, due to energy conservation and according to the Bernoulli principle, the pressure inside the collapsible tube P3 is smaller than the upstream pressure P1. For certain diameters of the collapsible tube 4219, the pressure inside the collapsible tube can be within the range of the central venous pulsatile pressure.

When the central venous pressure P2 is higher than P3 the tube collapses and flow is halted.

This in turn causes reduction in the central venous pressure. When the central venous pressure reduces below P3 the flow through the restriction is resumed.

Figure 45:
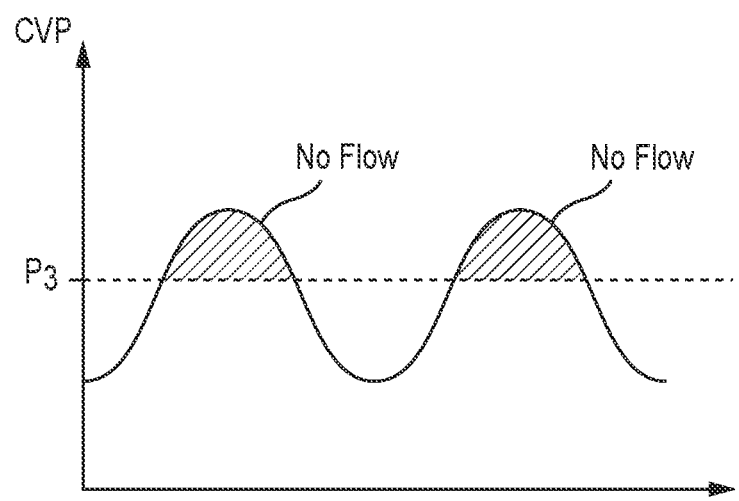
FIG. 45 graphs central venous pressure (CVP).

FIG. 45 shows a graph of central venous pressure (CVP).

Figure 46:
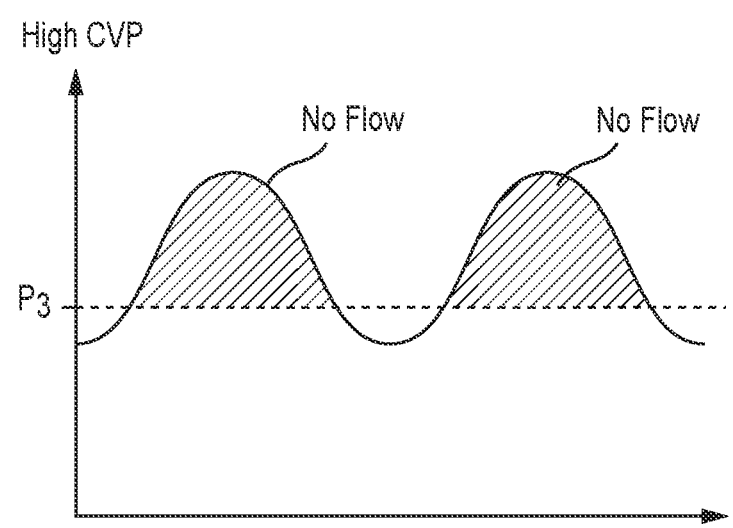
FIG. 46 illustrates elevated CVP.

FIG. 46 illustrates average CVP being higher than P3.

If the average CVP is higher than P3, the episodes of tube collapse will be longer and thus in turn will generate bigger reduction in the CVP. Such pulsatile restriction can also contribute to elimination of flow stagnation areas and thus reduce the risk of thrombus formation. In various embodiments, the restriction can either be total or partial. In preferred embodiments, the level of restriction is adjusted and pressure monitored until the required CVP is obtained to levels between −5 mm Hg to +5 mm Hg.

The disclosure provides methods and device for the treatment of edema with embodiments disclosed for the application to an outside of a body and invasive embodiments included in the disclosure. In certain preferred embodiments, the disclosure provides devices for treating edema. The devices include an extended collar member dimensioned to extend at least partway around a neck of a patient and a projection protruding inward from an inner surface of the collar member, the projection positioned to press against the neck near a jugular vein, thereby restricting blood flow within the jugular vein. Devices of the disclosure may further include one or more pressure sensing transducers to monitor the CVP and control the restrictions. Devices and methods of the disclosure may be used for reducing venous pressure and right ventricular end diastolic pressure. Preferably, devices and methods of the disclosure are used for reducing the pressure in the outflow of the lymphatic ducts and consequently enhancing lymphatic return in fluid overloaded patients. Devices and methods of the disclosure are beneficial for reducing pressures in the renal veins and improving flow across the kidneys and therefore improving urine output in fluid overloaded patients.

Certain embodiments include systems and methods that combine an internal device with an external device and use the internal device and the external device in combination. External devices include the device 101, the screw-based device 501, the disc-based device 1001, the balloon device 1401, the inflatable collar 1901, the tightening cuff style fastening device 2301, and the limb-cuff device 2701. Internal devices include the deployable stent device 3201, the open-sheath device 3401, the intravascular restriction device 3501, and the collapsible tube device 4201. Thus, certain aspects of the disclosure provide a system or kit for treating edema, wherein the system or kit includes an internal device and an external device. The internal device and the external device may each be, for example, any one of those embodiments disclosed herein. Related aspects provide a method thus uses such a system or kit for the treatment of edema.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of draining lymph, the method comprising: restricting flow through a jugular vein of a patient affected by heart failure or edema by applying pressure to a neck of the patient at a spot on the neck proximal to the jugular vein with a medical device for treating edema, the medical device comprising:
    an extended collar member dimensioned to extend at least partway around the neck,
    a screw threaded through a portion of the collar member, and
    a projection provided by a tip of the screw protruding inward from an inner surface of the collar member and positioned to press against the spot on the neck,
wherein the method includes twisting a head of the screw when the extended collar member is disposed about the neck of the patient to drive the projection into the neck to restrict flow within the jugular vein, thereby decreasing pressure at an outflow of a lymphatic duct.

2. The method of claim 1, further comprising imaging at least a portion of the jugular vein with a medical imaging instrument and using the imaging while applying the pressure to the spot on the neck.

3. The method of claim 1, further comprising restricting flow through the jugular vein by applying, with the projection, pressure to the jugular vein.

4. The method of claim 3, wherein restricting the flow through the jugular vein creates a local decrease in pressure within the jugular vein near the outlet of a lymphatic duct.

5. The method of claim 1, wherein the extended collar member forms a neck cuff that fastens around the neck.

6. The method of claim 1, wherein the extended collar member includes a C-shaped semi-ring that extends about halfway around the neck.

7. A method of draining lymph, the method comprising:
creating, within a jugular vein, a local decrease in pressure near an outlet of a lymphatic duct by applying pressure to a neck of the patient at a spot on the neck proximal to the jugular vein using a medical device for treating edema, wherein the device includes:

an extended collar member dimensioned to extend at least partway around the neck, a screw threaded through a portion of the collar member, wherein a tip of the screw provides a projection protruding inward from an inner surface of the collar member, the projection positioned to press against the spot on the neck, wherein the method includes twisting a head of the screw when the collar member is disposed about the neck of the patient to drive the projection into the neck to restrict flow within the jugular vein, thereby causing lymph to drain from interstitium and into a venous system of a patient.

8. The method of claim 7, wherein the extended collar member forms a neck cuff that fastens around the neck.

9. The method of claim 7, wherein the extended collar member includes a C-shaped semi-ring that extends about halfway around the neck.

\* \* \* \* \*